(12) United States Patent
Vail

(10) Patent No.: US 10,077,324 B2
(45) Date of Patent: Sep. 18, 2018

(54) POLYMERS, PREPARATION AND USE THEREOF

(71) Applicant: KCI Licensing, Inc., San Antonio, TX (US)

(72) Inventor: Neal Vail, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 114 days.

(21) Appl. No.: 14/766,191

(22) PCT Filed: Jan. 14, 2014

(86) PCT No.: PCT/US2014/011391
§ 371 (c)(1),
(2) Date: Aug. 6, 2015

(87) PCT Pub. No.: WO2014/123665
PCT Pub. Date: Aug. 14, 2014

(65) Prior Publication Data
US 2016/0108144 A1 Apr. 21, 2016

Related U.S. Application Data

(60) Provisional application No. 61/761,437, filed on Feb. 6, 2013.

(51) Int. Cl.
*C08F 28/02* (2006.01)
*C08G 83/00* (2006.01)
*A61L 24/00* (2006.01)
*A61L 24/04* (2006.01)

(52) U.S. Cl.
CPC .......... *C08F 28/02* (2013.01); *A61L 24/0015* (2013.01); *A61L 24/043* (2013.01); *C08G 83/00* (2013.01)

(58) Field of Classification Search
CPC .... A61L 24/0015; A61L 24/043; C08F 28/02; C08G 83/00
USPC ....................................................... 526/286
See application file for complete search history.

(56) References Cited

U.S. PATENT DOCUMENTS

| | | | |
|---|---|---|---|
| 3,361,723 A | 1/1968 | Ephraim | |
| 3,458,460 A | 7/1969 | Shepard et al. | |
| 3,879,471 A | 4/1975 | Farber | |
| 3,947,396 A | 3/1976 | Kangas et al. | |
| 3,950,296 A | 4/1976 | Kangas et al. | |
| 4,767,463 A | 8/1988 | Brode et al. | |
| 4,913,743 A | 4/1990 | Brode et al. | |
| 4,977,049 A * | 12/1990 | Kato .................... | G03G 5/0592 430/49.6 |
| 5,529,914 A | 6/1996 | Hubbell et al. | |
| 5,856,308 A | 1/1999 | St. Pierre et al. | |
| 6,283,384 B1 | 9/2001 | Wyant et al. | |
| 6,312,725 B1 | 11/2001 | Wallace et al. | |
| 6,428,978 B1 | 8/2002 | Olsen et al. | |
| 6,497,729 B1 | 12/2002 | Moussy et al. | |
| 6,568,398 B2 | 5/2003 | Cohen | |
| 6,916,488 B1 | 7/2005 | Meier et al. | |
| 7,514,531 B2 | 4/2009 | Xu et al. | |
| 7,622,533 B2 | 11/2009 | Lee | |
| 8,283,384 B2 | 10/2012 | Stewart et al. | |
| 2001/0056301 A1 | 12/2001 | Goupil et al. | |
| 2002/0006886 A1 | 1/2002 | Beerse et al. | |
| 2002/0164364 A1 | 11/2002 | Quong | |
| 2002/0169476 A1 | 11/2002 | Cohen | |
| 2003/0023000 A1 | 1/2003 | Bavouzet et al. | |
| 2004/0013738 A1 | 1/2004 | Voigt et al. | |
| 2004/0086479 A1 | 5/2004 | Grinstaff et al. | |
| 2005/0020734 A1 | 1/2005 | Asgarzadeh et al. | |
| 2005/0147580 A1 | 7/2005 | Connor et al. | |
| 2005/0220751 A1 | 10/2005 | Charmot et al. | |
| 2005/0281883 A1 | 12/2005 | Daniloff et al. | |
| 2006/0007528 A1 | 1/2006 | Cao et al. | |
| 2006/0015083 A1 | 1/2006 | Munro et al. | |
| 2006/0039950 A1 | 2/2006 | Zhou et al. | |
| 2006/0116682 A1 | 6/2006 | Longo | |
| 2006/0122290 A1 | 6/2006 | Hubbell et al. | |
| 2006/0156954 A1 | 7/2006 | Li et al. | |
| 2006/0183848 A1 | 8/2006 | Maier et al. | |
| 2006/0240064 A9 | 10/2006 | Hunter et al. | |
| 2006/0241242 A1 | 10/2006 | Devlin et al. | |
| 2006/0275337 A1 | 12/2006 | Cohen Stuart et al. | |
| 2006/0276371 A1 | 12/2006 | Schreiner et al. | |

(Continued)

FOREIGN PATENT DOCUMENTS

| | | |
|---|---|---|
| CN | 1341032 A | 3/2002 |
| CN | 1446590 A | 10/2003 |

(Continued)

OTHER PUBLICATIONS

Hu et al. (Synthesis and characterization of biodegradable and biocompatible amphiphilic block copolymers bearing pendant amino acid residues, Polymer 50 (2009) 4175-4181).*
Frey et al. (Poly(ethylene glycol-co-allyl glycidyl ether)s: A PEG-Based Modular Synthetic Platform for Multiple Bioconjugation, Bioconjugate Chem. 2011, 22, 436-444).*
Argenta et al., Vacuum-assisted closure: a new method for wound control and treatment: clinical experience. Ann Plast Surg. Jun. 1997;38(6):563-76.

(Continued)

*Primary Examiner* — Wenwen Cai
(74) *Attorney, Agent, or Firm* — McCarter & English, LLP; Matthew R. Van Eman

(57) ABSTRACT

The present teachings provide novel polymers, and methods of preparing and using thereof. The novel polymers each includes a sulfide, sulfonyl, or sulfonyl bond. The novel polymer are used to make polycations and/or polyanions, which can be used, for example, to produce adhesive complex coacervates.

Figure 1:
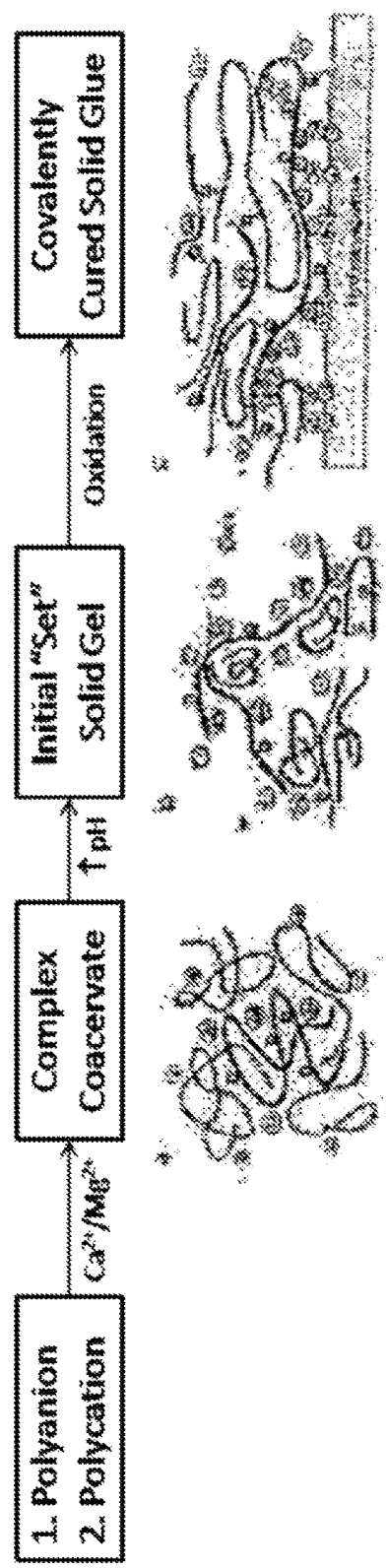

12 Claims, 2 Drawing Sheets
Specification includes a Sequence Listing.

(56) References Cited

U.S. PATENT DOCUMENTS

| | | | |
|---|---|---|---|
| 2007/0020469 A1 | 1/2007 | Wood et al. | |
| 2007/0077276 A1 | 4/2007 | Haynie | |
| 2007/0085059 A1 | 4/2007 | Mora-Gutierrez et al. | |
| 2007/0191273 A1 | 8/2007 | Ambati et al. | |
| 2007/0196454 A1 | 8/2007 | Stockman et al. | |
| 2007/0281904 A1 | 12/2007 | Baker et al. | |
| 2008/0003288 A1 | 1/2008 | Bromberg et al. | |
| 2008/0075778 A1 | 3/2008 | Heller | |
| 2008/0084000 A1 | 4/2008 | Forster | |
| 2009/0162407 A1 | 6/2009 | Biggs et al. | |
| 2010/0056474 A1 | 3/2010 | Baker et al. | |
| 2010/0120923 A1 | 5/2010 | Stewart et al. | |
| 2010/0291169 A1 | 11/2010 | Toreki et al. | |
| 2010/0305626 A1 | 12/2010 | Stewart et al. | |
| 2011/0054392 A1 | 3/2011 | Nies | |
| 2011/0287067 A1* | 11/2011 | Stewart | A61L 24/0015 424/400 |
| 2011/0288274 A1 | 11/2011 | Russell et al. | |
| 2012/0177918 A1 | 7/2012 | Stewart | |
| 2013/0129787 A1 | 5/2013 | Stewart | |
| 2013/0189313 A1 | 7/2013 | Stewart et al. | |
| 2013/0273145 A1 | 10/2013 | Vail | |
| 2014/0220082 A1* | 8/2014 | Stewart | C09J 133/26 424/400 |
| 2014/0287061 A1 | 9/2014 | Landolina | |
| 2015/0038400 A1 | 2/2015 | Vail | |
| 2015/0119353 A1 | 4/2015 | Vail | |

FOREIGN PATENT DOCUMENTS

| | | |
|---|---|---|
| CN | 101405037 A | 4/2009 |
| DE | 19810965 A1 | 9/1999 |
| EP | 0632329 B1 | 12/1997 |
| JP | 2002-166158 A | 6/2002 |
| JP | 2003-280056 A | 10/2003 |
| JP | 2009-084224 A | 4/2009 |
| JP | 2009-084292 A | 4/2009 |
| WO | 1995/006056 A1 | 3/1995 |
| WO | 2002/092217 A1 | 11/2002 |
| WO | 2002/100453 A1 | 12/2002 |
| WO | 2005/019421 A2 | 3/2005 |
| WO | 2007/024972 A2 | 3/2007 |
| WO | 2007/030811 A2 | 3/2007 |
| WO | 2009/094060 A1 | 7/2009 |
| WO | 2011/006595 A1 | 1/2011 |
| WO | 2011/011658 A1 | 1/2011 |
| WO | 2011/028967 A1 | 3/2011 |
| WO | 2011/106595 A1 | 9/2011 |
| WO | 2011/149907 A1 | 12/2011 |
| WO | 2012/065148 A2 | 5/2012 |
| WO | 2013/003400 A1 | 1/2013 |

OTHER PUBLICATIONS

Berg et al., The thermal transition of a non-hydroxylated form of collagen. Evidence for a role for hydroxyproline in stabilizing the triple-helix of collagen. Biochem Biophys Res Commun. May 1, 1973;52(1):115-20.
Blackburn et al., Negative-pressure dressings as a bolster for skin grafts. Ann Plast Surg. May 1998;40(5):453-7.
Chariker et al., Effective management of incisional and cutaneous fistulae with closed suction wound drainage. Contemporary Surgery. Jun. 1989;34:59-63.
Chinn et al., Closed wound suction drainage. J Foot Surg. Jan.-Feb. 1985;24(1):76-81.
Dattilo et al., Medical Textiles: Application of an Absorbable Barbed Bi-directional Surgical Suture. Journal of Textile and Apparel, Technology and Management. JTATM. 2002;2(2):1-5.
DeFranzo et al., Vacuum-assisted closure for the treatment of abdominal wounds. Clin Plast Surg. Apr. 2006;33 (2):213-24, vi.
Deng et al., Preparation and characterization of hyaluronanfchitosan scaffold cross-linked by 1-ethyl-3-(3-dimethylaminopropyl) carbodiimide. Polymer International. 2007;56:738-745.

Flack et al., An economic evaluation of VAC therapy compared with wound dressings in the treatment of diabetic foot ulcers. J Wound Care. Feb. 2008;17(2):71-8.
Hwang et al., Expression of functional recombinant mussel adhesive protein Mgfp-5 in *Escherichia coli*. Appl Environ Microbiol. Jun. 2004;70(6):3352-9.
Kamachi et al., Synthesis of Block Polymers for Desalination Membranes. Preparation of Block Copolymers of 2-Vinylpyridine and Methacrylic Acid or Acrylic Acid. Macromolecules. 1972;5(2):161-167.
Kayitmazer et al., Mesophase Separation and Probe Dynamics in Protein-Polyelectrolyte Coacervates. Chemical Engineering Faculty Publications. 2007;3:1064-1076.
KCI Medical Products (UK) Ltd., V.A.C. Therapy Safety Information. pp. 1-4. (2007).
Lee et al. Rapid Gel Formation and Adhesion in Photocurable and Biodegradable Block Copolymers with High DOPA content. Macromolecules. 2006;39(5):1740-1748.
Lee et al., Single-molecule mechanics of mussel adhesion. Proc Natl Acad Sci U S A. Aug. 29, 2006;103 (35):12999-3003.
Lee et al., Synthesis of 3,4-dihydroxyphenylalanine (DOPA) containing monomers and their co-polymerization with PEG-diacrylate to form hydrogels. J Biomater Sci Polym Ed. 2004;15(4):449-64.
Lim et al., The adhesive properties of coacervated recombinant hybrid mussel adhesive proteins. Biomaterials. May 2010;31(13):3715-22.
Liu et al., Chemistry of periodate-mediated cross-linking of 3,4-dihydroxylphenylalanine-containing molecules to proteins. J Am Chem Soc. Nov. 29, 2006;128(47)15228-35.
Masters, Reliable, inexpensive and simple suction dressings. Br J Plast Surg. Apr. 1998;51(3):267.
Mo et al., Soft tissue adhesive composed of modified gelatin and polysaccharides. J Biomater Sci Polym Ed. 2000;11 (4):341-51.
Nippon Shokubai Co., Ltd., Polyethyleneimine: EPOMIN. https://www.shokubai.co.jp/en/products/functionality/?epomin1.html. 10 pages (Feb. 28, 2014).
O'Connor et al., Vacuum-assisted closure for the treatment of complex chest wounds. Ann Thorac Surg. Apr. 2005;79 (4):1196-200.
Shao et al., A water-borne adhesive modeled after the sandcastle glue of P. californica. Macromol Biosci. May 13, 2009;9(5):464-71.
Stevens et al., Multiscale structure of the underwater adhesive of Phragmatopoma californica: a nanostructured latex with a steep microporosity gradient. Langmuir. Apr. 24, 2007;23(9):5045-9.
Stewart et al., The tube cement of Phragmatopoma californica: a solid foam. J Exp Biol. Dec. 2004;207(Pt 26):4727-34.
Wang et al., A Novel Bioadhesive Protein of Silk Filaments Spun Underwater by Caddisfly Larvae. Advanced Materials Research. 2009;79/82:1631-1634.
Wikipedia. Collagen. https://web.archive.org/web/20150211164108/http://en.wikipedia.org/wiki/Collagen. 26 pages. (2015).
Wikipedia. Gelatin. https://web.archive.org/web/20150211071640/https://en.wikipedia.org/wiki/Gelatin. 9 pages. (2015).
Yu et al., Synthetic Polypeptide Mimics of Marine Adhesives. Macromolecules. Jul. 28, 1998;31(15):4739-45.
Zhao et al., Cement proteins of the tube-building polychaete Phragmatopoma califomica. J Biol Chem. Dec. 30, 2005;280(52):42938-44.
Chinese Office Action for Application No. 200880128307.2, dated Oct. 27, 2011. 13 pages.
Supplementary Extended European Search Report for Application No. 08871349.0 dated Nov. 14, 2011. 4 pages.
International Preliminary Report on Patentability for Application No. PCT/US2008/083311, dated Jul. 27, 2010. 10 pages.
International Search Report and Written Opinion for Application No. PCT/US2011/037697, dated Sep. 13, 2011. 3 pages.
International Search Report and Written Opinion for Application No. PCT/US/2011/060500, dated Jul. 5, 2012. 18 pages.
Written Opinion for Application No. PCT/US2011/26169, dated May 17, 2011. 7 pages.
International Search Report for Application No. PCT/US2013/027107, dated Sep. 27, 2013. 6 pages.

(56) References Cited

OTHER PUBLICATIONS

International Preliminary Report on Patentability for Application No. PCT/US2013/027107, dated Sep. 4, 2014. 10 pages.
International Search Report for Application No. PCT/US2013/029131, dated Aug. 26, 2013. 4 pages.
International Preliminary Report on Patentability for Application No. PCT/US2013/029131, dated Sep. 18, 2014. 3 pages.
International Search Report for Application No. PCT/US2014/011391, dated Jun. 5, 2014. 6 pages.
International Preliminary Report on Patentability for Application No. PCT/US2014/011391, dated Aug. 20, 2015. 10 pages.

\* cited by examiner

POLYMERS, PREPARATION AND USE THEREOF

This application is a 35 U.S.C. § 371 national stage filing of International Application No. PCT/US2014/011391, filed on Jan. 14, 2014, which claims priority under 35 U.S.C. § 119 to U.S. Provisional Application No. 61/761,347, which was filed on Feb. 6, 2013, the content of each are herein incorporated in its entirety.

SUBMISSION OF SEQUENCE LISTING

The Sequence Listing associated with this application is filed in electronic format via. EFS-Web and hereby incorporated by reference into the specification in its entirety. The name of the text file containing the Sequence Listing is 123436_17602_Revised_Sequence_Listing. The size of the text file is 9 KB, and the text file was created on Nov. 11, 2015.

The present teachings provide novel polymers and/or methods of preparing and using thereof. For example, the novel polymers can be used to produce polycations and/or polyanions, which can be used, for example, to produce complex coacervates.

In one aspect, the present teachings relate to a polymer having a sulfide, sulfinyl, or sulfonyl. In various embodiments, the polymer comprises a branch having a sulfide, sulfinyl, or sulfonyl. For example, the polymer can have Formula I:

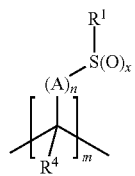

I wherein $R^1$, $R^4$, A, m, n, and x are as defined herein.

In another aspect, the present teachings relate to methods of preparing or using the polymers.

In another aspect, the present teachings relate to a polycation or a polyanion. In various embodiments, the polycation or polyanion comprises a polymer described herein.

In another aspect, the present teachings relate to a coacervate. In various embodiments, the coacervate comprises a polycation and/or a polyanion disclosed herein. In some embodiments, the coacervate is used as an adhesive.

In another aspect, the present teachings relate to methods of making and using coacervates described herein. For example, the coacervate can be used as an adhesive in the presence of water.

FIG. 1 illustrates an example of the formation of complex coacervates: (a) a polycation is combined with a polyanion in the presence of metal cations; (b) a polyanion is paired with the polycation to form a first complex coacervate; (c) a second complex coacervate (e.g., an "initial 'set' solid gel") is formed, for example, by changing the pH of the first complex coacervate; and (d) a third complex coacervate (e.g., a "covalently cured solid glue") is formed, for example, by crosslinking the second complex coacervate.

Figure 2:
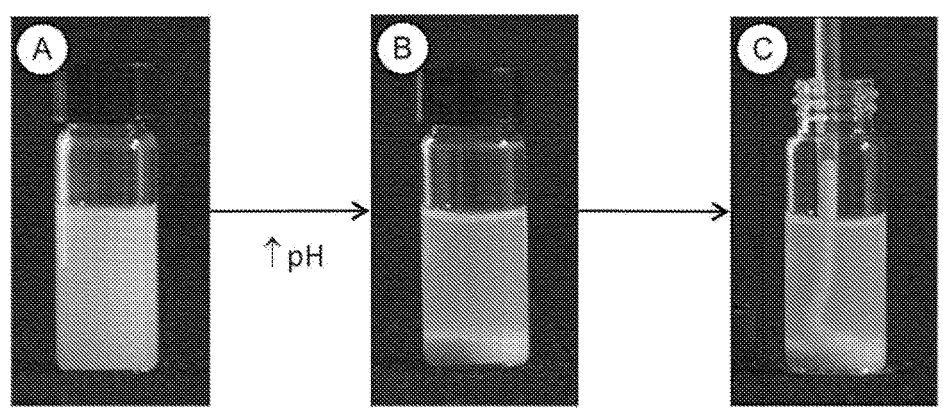

FIG. 2. illustrates the formation of two exemplary complex coacervates: (a) a first complex coacervate was formed by combining polycations and polyanions; (b) a second complex coacervate was formed, for example, by raising the pH of the first complex coacervate; and (c) the second complex coacervate exhibited certain properties, for example, having a density greater than water, immiscibility in water, and the ability to adhere to an object.

Reference will be made to certain exemplary embodiments according to the present teachings, certain examples of which are illustrated in the accompanying drawings. It will be understood that both the description, the references to certain exemplary embodiments, and the drawings are not restrictive.

As used herein, phrases and symbols are generally intended to have the meanings as set forth below, except to the extent that the context in which they are used indicates otherwise.

As used herein, the articles "a", "an", and "the" include plural referents unless expressly and unequivocally limited to one referent. For example, reference to "a compound" includes a mixture of two or more compounds, and reference to "a pharmaceutically acceptable carrier" includes a mixture of one or more carriers, and the like. Accordingly, unless otherwise specified, the articles "a", "an", and "the" can have the same meanings as the term "one or more" or "at least one."

It should also be noted that the term "or" generally includes "and/or" unless the context clearly dictates otherwise.

Unless otherwise specified, the chemical groups refer to their unsubstituted and substituted forms. For example, "alkyl", unless otherwise specified, encompasses both "unsubstituted alkyl" and "substituted alkyl". By "optional" or "optionally", it is meant that the subsequently described event or circumstance may or may not occur, and that the description includes instances in which is does not. For example, "optionally substituted aryl" encompasses both "unsubstituted aryl" and "substituted aryl" as defined below. It will be understood by those skilled in the art, with respect to any group containing one or more substituents, that such groups are not intended to introduce any substitution or substitution patterns that are sterically impractical, synthetically unfeasible, and/or inherently unstable.

Unless otherwise specified, the chemical groups include their corresponding monovalent and multivalent groups. For example, methyl include monovalent methyl (—$CH_3$), divalent methyl (—$CH_2$—, methylyl), trivalent methyl

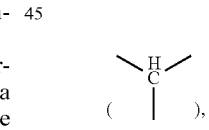

teravalent methyl

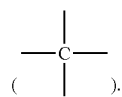

Unless otherwise specified, all numbers expressing quantities of ingredients, reaction conditions, and other properties or parameters used in the specification and claims are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

All numerical ranges herein include all numerical values and ranges of all numerical values within the recited range of numerical values. Further, while the numerical ranges and parameters setting forth the broad scope of the disclosure are approximations as discussed above, the numerical values set forth in the Examples section are reported as precisely as possible. It should be understood, however, that such numerical values inherently contain certain errors resulting from the measurement equipment and/or measurement technique.

"Compounds" refers to compounds encompassed by structural formulae described herein and includes any specific compounds within the formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan.

For the purposes of the present teachings, "chiral compounds" are compounds having at least one center of chirality (i.e., at least one asymmetric atom, in particular, at least one asymmetric C atom), having an axis of chirality, a plane of chirality, or a screw structure. "Achiral compounds" are compounds that are not chiral.

Compounds described herein include, but are not limited to, optical isomers of the polyanionic and polycationic compound described herein, racemates thereof, and other mixtures thereof. In such embodiments, the single enantiomers or diastereomers, i.e., optically active forms can be obtained by asymmetric synthesis or by resolution of the racemates. Resolution of the racemates can be accomplished, for example, by conventional methods such as crystallization in the presence of a resolving agent, or chromatography using, for example, a chiral high-pressure liquid chromatography (HPLC) column. However, unless otherwise stated, it should be assumed that the polyanionic and polycationic compounds described herein cover all asymmetric variants, including isomers, racemates, enantiomers, diastereomers, and other mixtures thereof. In addition, the polyanionic and polycationic compounds described herein include Z- and E-forms (e.g., cis- and trans-forms) of compounds with double bonds. In embodiments in which the polyanionic and polycationic compounds described herein exist in various tautomeric forms, compounds provided by the present disclosure include all tautomeric forms of the compound.

The term "alkyl" as used herein refers to a saturated straight or branched hydrocarbon, such as a straight or branched group of 1 to 22, 1 to 8, or 1 to 6 carbon atoms, referred to herein as $(C_1-C_{22})$alkyl, $(C_1-C_8)$alkyl, or $(C_1-C_6)$alkyl, respectively. The alkyl groups can be substituted with one or more groups each independently selected from alkyl, alkenyl, alkynyl, aryl, arylalkyl, alkoxy, aryloxy, cycloalkyl, heteroaryl, heterocyclyl, halogen, cyano, hydroxyl, oxo, amino, imino, phosphate, sulfide, sulfinyl, sulfonyl, and sulfonic acid, and each of the alkyl, alkenyl, alkynyl, aryl, arylalkyl, alkoxy, aryloxy, cycloalkyl, heteroaryl, and heterocyclyl optionally can be substituted with one or more suitable substituents as described herein. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkenyl" as used herein refers to an unsaturated straight or branched hydrocarbon having at least one carbon-carbon double bond, such as a straight or branched group of 2 to 22, 2 to 8, or 2 to 6 carbon atoms, referred to herein as $(C_2-C_{22})$alkenyl, $(C_2-C_8)$alkenyl, or $(C_2-C_6)$alkenyl, respectively. The alkenyl groups can be substituted with one or more groups each independently selected from alkyl, alkenyl, alkynyl, aryl, arylalkyl, alkoxy, aryloxy, cycloalkyl, heteroaryl, heterocyclyl, halogen, cyano, hydroxyl, oxo, amino, imino, phosphate, sulfide, sulfinyl, sulfonyl, and sulfonic acid, and each of the alkyl, alkenyl, alkynyl, aryl, arylalkyl, alkoxy, aryloxy, cycloalkyl, heteroaryl, and heterocyclyl optionally can be substituted with one or more suitable substituents as described herein. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, etc.

The term "alkynyl" as used herein refers to an unsaturated straight or branched hydrocarbon having at least one carbon-carbon triple bond, such as a straight or branched group of 2 to 22, 2 to 8, or 2 to 6 carbon atoms, referred to herein as $(C_2-C_{22})$alkynyl, $(C_2-C_8)$alkynyl, or $(C_2-C_6)$alkynyl, respectively. The alkynyl groups can be substituted with one or more groups each independently selected from alkyl, alkenyl, alkynyl, aryl, arylalkyl, alkoxy, aryloxy, cycloalkyl, heteroaryl, heterocyclyl, halogen, cyano, hydroxyl, oxo, amino, imino, phosphate, sulfide, sulfinyl, sulfonyl, and sulfonic acid, and each of the alkyl, alkenyl, alkynyl, aryl, arylalkyl, alkoxy, aryloxy, cycloalkyl, heteroaryl, and heterocyclyl optionally can be substituted with one or more suitable substituents as described herein. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl, etc.

The term "alkoxy" as used herein refers to an alkyl group attached to an oxygen (—O-alkyl). "Alkoxy" groups also include an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1 to 22, 1 to 8, or 1 to 6 carbon atoms, referred to herein as $(C_1-C_{22})$alkoxy, $(C_1-C_8)$alkoxy, or $(C_1-C_6)$alkoxy, respectively. The alkoxy groups can be substituted with one or more groups each independently selected from alkyl, alkenyl, alkynyl, aryl, arylalkyl, alkoxy, aryloxy, cycloalkyl, heteroaryl, heterocyclyl, halogen, cyano, hydroxyl, oxo, amino, imino, phosphate, sulfide, sulfinyl, sulfonyl, and sulfonic acid, and each of the alkyl, alkenyl, alkynyl, aryl, arylalkyl, alkoxy, aryloxy, cycloalkyl, heteroaryl, and heterocyclyl optionally can be substituted with one or more suitable substituents as described herein. Exemplary alkoxy groups include, but are not limited to, methoxy, ethoxy, alloxy, propynyloxy, etc.

The term "aryl" as used herein refers to a mono-, bi-, or other multi-carbocyclic aromatic ring system. The aryl group can optionally be fused to one or more rings selected from aryls, cycloalkyls, and heterocyclyls. The aryl groups can be substituted with one or more groups each independently selected from alkyl, alkenyl, alkynyl, aryl, arylalkyl, alkoxy, aryloxy, cycloalkyl, heteroaryl, heterocyclyl, halogen, cyano, hydroxyl, oxo, amino, imino, phosphate, sulfide, sulfinyl, sulfonyl, and sulfonic acid, and each of the alkyl, alkenyl, alkynyl, aryl, arylalkyl, alkoxy, aryloxy, cycloalkyl, heteroaryl, and heterocyclyl optionally can be substituted with one or more suitable substituents as described herein. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "$(C_6)$aryl."

The term "arylalkyl" as used herein refers to an alkyl group having at least one aryl substituent, e.g., aryl-alkyl-. Exemplary arylalkyl groups include, but are not limited to, arylalkyls having a monocyclic aromatic ring system, wherein the ring comprises 6 carbon atoms, referred to herein as "$(C_6)$arylalkyl." The term "benzyl" as used herein refers to the group phenyl-$CH_2$—.

The term "aryloxy" as used herein refers to an aryl group attached to an oxygen atom. Exemplary aryloxy groups include, but are not limited to, aryloxys having a monocyclic aromatic ring system, wherein the ring comprises 6 carbon atoms, referred to herein as "$(C_6)$aryloxy."

The term "cycloalkyl" as used herein refers to a saturated or unsaturated cyclic, bicyclic, or bridged bicyclic hydrocarbon group of 3-12 carbons or 3-8 carbons, referred to herein as "$(C_3$-$C_{12})$cycloalkyl" or "$(C_3$-$C_8)$cycloalkyl," respectively. The cycloalkyl groups can be substituted with one or more groups each independently selected from alkyl, alkenyl, alkynyl, aryl, arylalkyl, alkoxy, aryloxy, cycloalkyl, heteroaryl, heterocyclyl, halogen, cyano, hydroxyl, oxo, amino, imino, phosphate, sulfide, sulfinyl, sulfonyl, and sulfonic acid and each of the alkyl, alkenyl, alkynyl, aryl, arylalkyl, alkoxy, aryloxy, cycloalkyl, heteroaryl, and heterocyclyl optionally can be substituted with one or more suitable substituents as described herein. Exemplary cycloalkyl groups include, but are not limited to, cyclohexyl, cyclohexenyl, cyclopentyl, and cyclopentenyl. Cycloalkyl groups can be fused to other cycloalkyl saturated or unsaturated, aryl, or heterocyclyl groups.

The term "heteroaryl" as used herein refers to a mono-, bi-, or multi-cyclic aromatic ring system containing one or more heteroatoms, for example, 1 to 3 heteroatoms, such as nitrogen, oxygen, and sulfur. The heteroaryl groups can be substituted with one or more groups each independently selected from alkyl, alkenyl, alkynyl, aryl, arylalkyl, alkoxy, aryloxy, cycloalkyl, heteroaryl, heterocyclyl, halogen, cyano, hydroxyl, oxo, amino, imino, phosphate, sulfide, sulfinyl, sulfonyl, and sulfonic acid, and each of the alkyl, alkenyl, alkynyl, aryl, arylalkyl, alkoxy, aryloxy, cycloalkyl, heteroaryl, and heterocyclyl optionally can be substituted with one or more suitable substituents as described herein. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)- triazolyl, pyrazinyl, pyrimidilyl, tetrazolyl, furyl, thienyl, isoxazolyl, thiazolyl, furyl, isoxazolyl, and oxazolyl. Exemplary heteroaryl groups include, but are not limited to, a monocyclic aromatic ring, wherein the ring comprises 2 to 5 carbon atoms and 1 to 3 heteroatoms, referred to herein as "$(C_2$-$C_5)$heteroaryl."

The terms "heterocycle," "heterocyclyl," or "heterocyclic" as used herein refer to a saturated or unsaturated 3-, 4-, 5-, 6- or 7-membered ring containing one, two, or three heteroatoms independently selected from nitrogen, oxygen, and sulfur. Heterocycles can be aromatic (heteroaryls) or non-aromatic. The heterocycle, heterocyclyl, or heterocyclic groups can be substituted with one or more groups each independently selected from alkyl, alkenyl, alkynyl, aryl, arylalkyl, alkoxy, aryloxy, cycloalkyl, heteroaryl, heterocyclyl, halogen, cyano, hydroxyl, oxo, amino, imino, phosphate, sulfide, sulfinyl, sulfonyl, and sulfonic acid and each of the alkyl, alkenyl, alkynyl, aryl, arylalkyl, alkoxy, aryloxy, cycloalkyl, heteroaryl, and heterocyclyl optionally can be substituted with one or more suitable substituents as described herein. Heterocycles also include bicyclic, tricyclic, and tetracyclic groups in which any of the above heterocyclic rings is fused to one or two rings independently selected from aryls, cycloalkyls, and heterocycles.

The term "amine" or "amino" as used herein refers to the formula —$NR_dR_e$, where $R_d$ and $R_e$ independently are selected from hydrogen, alkyl, alkenyl, alkynyl, aryl, arylalkyl, cycloalkyl, and heterocyclyl. The amino can be attached to the parent molecular group through the nitrogen. The amino also may be cyclic, for example any two of $R_d$ and $R_e$ may be joined together or with the N to form a 3- to 12-membered ring, e.g., morpholino or piperidinyl. The term amino also includes the corresponding quaternary ammonium salt of any amino group, for example, —$(NR_dR_eR_f)^+$, where $R_d$, $R_e$, and $R_f$ independently are selected from hydrogen, alkyl, alkenyl, aryl, arylalkyl, cycloalkyl, and heterocyclyl. Exemplary amino groups include alkylamino groups, wherein at least one of $R_d$ and $R_e$ is an alkyl group. Each of the alkyl, alkenyl, aryl, arylalkyl, cycloalkyl, and heterocyclyl can be substituted with at least one suitable substituent as further described below.

The terms "halo" or "halogen" or "hal" or "halide" as used herein refers to F, Cl, Br, and I. The term "halide" as used herein can also refer to an ionic form of F, Cl, Br, or I. For example, chloride can mean —Cl or $Cl^-$.

The term "cyano" as used herein refers to —CN. The term "nitro" as used herein refers to —$NO_2$.

The term "oxo" as used herein refers to =O.

The term "hydroxyl" as used herein refers to —OH.

The term "imine" or "imino" as used herein refers to =$NR_g$, where $R_g$ is selected from hydrogen, alkyl, alkenyl, aryl, arylalkyl, cycloalkyl, and heterocyclyl. Each of the alkyl, alkenyl, aryl, arylalkyl, cycloalkyl, and heterocyclyl can be substituted with at least one suitable substituent as further described below.

The term "phosphate" as used herein refers to the structure —OP(O)(OH)$_2$, any one of its corresponding salts (e.g., —OP(O)(OH)ONa, —OP(O)(O)$_2$Na$_2$, —OP(O)(OH)OK, —OP(O)(O)$_2$K$_2$, etc.), or any one of its corresponding esters (e.g., —OP(O)(OH)(OR$_h$), —OP(O)(OR$_h$)$_2$, etc., where $R_h$ is alkyl, alkenyl, alkynyl, aryl, arylalkyl, cycloalkyl, heteroaryl, or heterocyclyl).

The term "phosphonate" as used herein refers to the structure —P(O)(OH)$_2$, any one of its corresponding salts (e.g., —P(O)(OH)ONa, —P(O)(O)$_2$Na$_2$, —P(O)(OH)OK, —P(O)(O)$_2$K$_2$, etc.) or any one of its esters (e.g., —P(O)

(OH)(OR$_h$), —P(O)(OR$_h$)$_2$, where R$_h$ is alkyl, alkenyl, alkynyl, aryl, arylalkyl, cycloalkyl, heteroaryl, or heterocyclyl). In some embodiments, R$_h$ is alkyl, alkenyl, aryl, arylalkyl, or cycloalkyl.

The term "sulfide" as used herein refers to the structure —S—, —R$_i$S—, —R$_i$SR$_j$—, or —SR$_j$—, where R$_i$ and R$_j$ each independently is alkyl, alkenyl, alkynyl, aryl, arylalkyl, cycloalkyl, haloalkyl, or heterocyclyl, where each of the alkyl, alkenyl, alkynyl, aryl, arylalkyl, cycloalkyl, haloalkyl, and heterocyclyl is optionally substituted. The sulfide may be cyclic, for example, forming a 3 to 12-membered ring. The term "alkylsulfide" as used herein refers to an alkyl group attached to a sulfur atom.

The term "sulfinyl" as used herein refers to the structure —S(O)—, —R$_k$S(O)—, —R$_k$S(O)R$_l$—, or —S(O)R$_l$—, wherein R$_k$ and R$_l$ each independently is alkyl, alkenyl, alkynyl, aryl, arylalkyl, cycloalkyl, haloalkyl, or heterocyclyl, where each of the alkyl, alkenyl, alkynyl, aryl, arylalkyl, cycloalkyl, haloalkyl, and heterocyclyl is optionally substituted. Exemplary sulfinyl groups include, but are not limited to, alkylsulfinyls wherein at least one of R$_k$ or R$_l$ is alkyl, alkenyl, or alkynyl.

The term "sulfonyl" as used herein refers to the structure —S(O)$_2$—, —R$_m$S(O)$_2$—, —R$_m$S(O)$_2$R$_n$—, or —S(O)$_2$R$_n$—, wherein R$_m$ and R$_n$ each independently is alkyl, alkenyl, alkynyl, aryl, arylalkyl, cycloalkyl, haloalkyl, or heterocyclyl, where each of the alkyl, alkenyl, alkynyl, aryl, arylalkyl, cycloalkyl, haloalkyl, and heterocyclyl is optionally substituted. Exemplary sulfonyl groups include, but are not limited to, alkylsulfonyls wherein at least one of R$_m$ or R$_n$ is alkyl, alkenyl, or alkynyl.

The term "sulfate" as used herein refers to —OSO$_2$OH, any one of its corresponding salts (e.g., —OSO$_3$Na, —OSO$_3$K, etc.), or any one of its corresponding esters (e.g., —OSO$_3$R$_h$, where R$_h$ is alkyl, alkenyl, alkynyl, aryl, arylalkyl, cycloalkyl, heteroaryl, or heterocyclyl).

The term "sulfonate" as used herein refers to —SO$_2$OH (also known as "sulfonic acid"), any one of its corresponding salts (e.g., —SO$_3$Na, —SO$_3$K, etc.), or any one of its corresponding esters (e.g., —SO$_3$R$_h$, where R$_h$ is alkyl, alkenyl, alkynyl, aryl, arylalkyl, cycloalkyl, heteroaryl, or heterocyclyl).

The term "borate" as used herein refers to —OB(OH)$_2$ or salts thereof.

The term "boronate" as used herein refers to —B(OH)$_2$, —OBR$_i$(OH), salts or esters thereof where R$_i$ is alkyl, alkenyl, alkynyl, aryl, arylalkyl, cycloalkyl, heteroaryl, or heterocyclyl.

Each of "suitable substituents" referred to herein is selected from alkyl, alkenyl, alkynyl, aryl, heteroaryl, cycloalkyl, heterocyclyl, heteroaryl, alkoxy, aryloxy, cyano, hydroxyl, oxo, imino, halo, amino, phosphate, phosphonate, sulfate, sulfonate, or borate. In some embodiments, each of the alkyl, alkenyl, and alkynyl described herein comprises 1 to 22, 1 to 8, or 1 to 6 carbon atoms. In some embodiments, the cycloalkyl described herein comprises 3 to 7 ring carbon atoms. In some embodiments, the aryl described herein comprises 6 to 10 ring carbon atoms. In some embodiments, the heterocyclyl or heteroaryl described herein each comprises 3 to 10 ring carbon atoms. In some embodiments, the alkoxy described herein comprises 1 to 22, 1 to 8, or 1 to 6 carbon atoms. In some embodiments, the aryloxy is phenoxy. In some embodiments, the amino is selected from —NH(C$_{1-22}$, C$_{1-8}$, or C$_{1-6}$ alkyl), —N(C$_{1-22}$, C$_{1-8}$, and C$_{1-6}$ alkyl)$_2$, —NH(pheny), and —N(phenyl)$_2$. In some embodiments, the suitable substituent is selected from imino, amino, phosphate, phosphonate, sulfate, sulfonate, and borate. One of ordinary skill in art can readily choose a suitable substituent based on the stability and synthetic activity of the compounds of the present teachings.

Accordingly, alkyl can be substituted with one or more hydroxyl groups to form "hydroxylalkyl," including 2-hydroxylpropyl

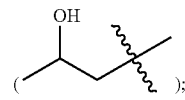

aryl group can be substituted with one or more hydroxyl groups to form "hydroxylaryl"; alkenyloxy (an alkoxy) can be substituted with an oxo to form unsubstituted and substituted acryloxy groups (e.g., acryloxy

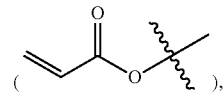

methacryloxy

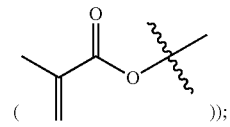 [SMILES: *OC(=O)C(=C)C]

and methylamino (an amino) can be substituted with an amino group and an imino group to form guanidino

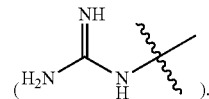

The term "pharmaceutically acceptable salt(s)" refers to salts of acidic or basic groups that may be present in compounds used in the present compositions. Compounds included in the present compositions that are basic in nature are capable of forming salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, malate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

"Antimicrobial activity" referred to herein means the ability to kill or inhibit the growth of microorganisms, including bacteria, yeasts, fungi, and protozoan.

In one aspect, the present teachings provide a polymer having a sulfide, sulfinyl, or sulfonyl. In various embodiments, the sulfide, sulfinyl, or sulfonyl is included in the backbone of the polymer. In various embodiments, the polymer comprises a branch having a sulfide, sulfinyl, or sulfonyl. For example, the polymer can have a polymer of Formula I:

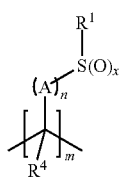

I wherein

A at each occurrence independently is O, $NR^2$, or $C(R^3)_2$;

$R^1$ or $R^2$ at each occurrence independently is hydrogen, alkyl, alkenyl, aryl, arylalkyl, cycloalkyl, heteroaryl, or heterocyclyl, wherein each of the alkyl, alkenyl, aryl, arylalkyl, cycloalkyl, heteroaryl, and heterocyclyl optionally is substituted with one or more suitable substituents;

$R^3$ at each occurrence is hydrogen, alkyl, alkenyl, aryl, arylalkyl, cycloalkyl, heteroaryl, heterocyclyl, hydroxyl, alkoxyl, aroxyl, ester, sulfide, sulfinyl, sulfonyl, halo, cyano, nitro, carbonyl, or carboxylate, wherein each of the alkyl, alkenyl, aryl, arylalkyl, cycloalkyl, heteroaryl, heterocyclyl, alkoxyl, aroxyl, ester, sulfide, sulfinyl, sulfonyl, carbonyl, and carboxylate optionally is substituted with one or more suitable substituents, or two $R^3$ groups are combined to form oxo or imino;

$R^4$ at each occurrence is hydrogen or alkyl;

x is 0, 1, or 2; and m and n, at each occurrence, each is an integer;

or a salt thereof.

In various embodiments, n at each occurrence is from 1 to 10. For example, n at each occurrence can be 1, 2, 3, 4, 5, 6, 7, 8, 9, or 10. In various embodiments, A at each occurrence independently is O or $C(R^3)_2$. In various embodiments, $R^3$ is hydrogen or optionally substituted alkyl.

In various embodiments, m is in the range of 20 to 6000.

In some embodiments, the polymer has a moiety of Formula II:

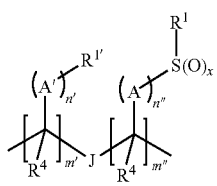

II wherein m', m", n', and n", at each occurrence, each is an integer;

J represents other parts of the polymer;

A' at each occurrence is O, $NR^2$, $C(R^3)_2$, or $CR^3$;

$R^{1'}$ at each occurrence is hydrogen, alkyl, alkenyl, aryl, arylalkyl, cycloalkyl, heteroaryl, or heterocyclyl, wherein each of the alkyl, alkenyl, aryl, arylalkyl, cycloalkyl, heteroaryl, and heterocyclyl optionally is substituted with one or more suitable substituents; and A, $R^2$, $R^3$, $R^4$, and x are as defined herein.

In various embodiments, at least one $R^{1'}$ comprises a vinyl or ethynyl group. In some embodiments, at least one $R^{1'}$ comprises a vinyl group.

In various embodiments, the sum of m' and m" is m. Without attempting to limit the scope of the present teachings, the ratio of m' to m" can be adjusted so that the polymer can have a certain percentage of the sulfide, sulfinyl, or sulfonyl moiety. For the purpose of illustration only and not an attempt to limit the scope of the present teachings, if the molar percentage of the sulfide, sulfinyl, or sulfonyl moiety is defined as $$\frac{m''}{(m' + m'')} \times 100\%,$$

it can range from about 1% to about 100%. In some embodiments, the percentage ranges from about 10% to about 90%, about 20% to about 80%, about 30% to about 70%, about 40% to about 60%, or about 50%. In some embodiments, the percentage is about 5%, about 10%, about 20%, about 30%, about 40%, about 50%, about 60%, about 70%, about 80%, about 90%, or about 100%.

In various embodiments, at least one A' is O. In some embodiments, $(A')_{n'}$ comprises $—OCH_2—$. In various embodiments, at least one A is O. In some embodiments, $(A)_{n''}$ comprises $—OCH_2—$, $—OCH_2CH_2—$, or $—OCH_2CH_2CH_2—$. In particular embodiments, $(A)_{n''}$ comprises $—OCH_2CH_2—$. In particular embodiments, $(A)_{n''}$ comprises $—OCH_2CH_2CH_2—$.

In certain embodiments, the polymer has Formula IIIa or IIIb:

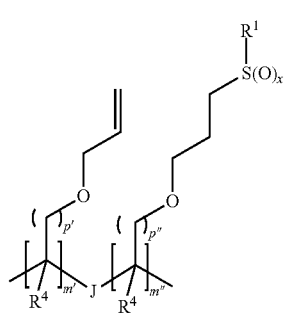

IIIa

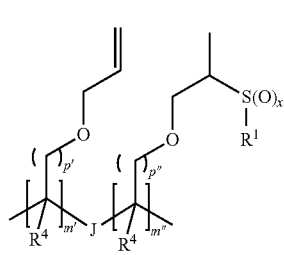

IIIb wherein p' and p", at each occurrence, each is an integer; and
J, $R^1$, $R^4$, m', m", and x are as defined herein.

In various embodiments, x is 0 (i.e., a sulfide). In various embodiments, p' is 1. In various embodiments, p" is 1.

In certain embodiments, the polymer has a moiety of Formula IVa or IVb:

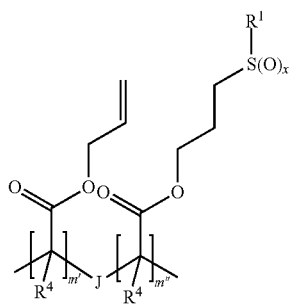

IVa

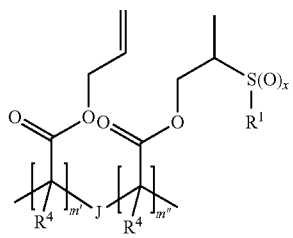

IVb wherein J, $R^1$, $R^4$, m', m", and x are as defined herein.

In some embodiments, x is 0.

Another aspect of the present teachings relates to a polycation comprising a polymer described herein. In various embodiments, the polycation has a formula selected from Formulae I, II, IIIA, IIIB, IVa, and IVb.

The polycation described herein generally comprises a polymer backbone with a plurality of cationic groups at a particular pH. In various embodiments, the polymer backbone is J. The cationic groups can be pendant to the polymer backbone (e.g., part of $R^1$), and/or incorporated within the polymer backbone (e.g., part of J). In various embodiments, the polycation is any biocompatible polymer possessing cationic groups or groups that can be readily converted to cationic groups, for example, by adjusting the pH.

In various embodiments, the polycation has analgesic effects, antitumor activity, anticoagulant activity, anticholesterolemic activity, antimicrobial activity, and/or antioxidative activity. In some embodiments, the polycation promotes cell interaction, including cell adhesion, cell migration, cell differentiation, and morphogenesis.

In various embodiments, the polycation comprises a polycarbon, a polyether, a polyamine, a polyamide, a polyester, or a natural polymer. For example, in some embodiments, J is a moiety comprising polycarbon, polyether, polyamine, polyamide, polyester, or natural polymer.

In some embodiments, the polycation comprises a polyether. For example, J can include a polyether moiety. In certain embodiments, J comprises a moiety selected from poly(t-butyl glycidyl ether), poly(ethoxyethyl glycidyl ether), and poly(allyl glycidyl ether). In particular embodiments, J comprises a poly(allyl glycidyl ether) (pAGE) moiety. For example, the polycation can have Formula V:

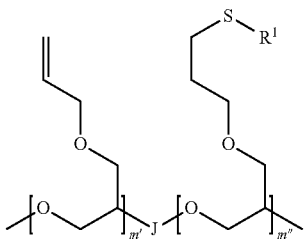

V wherein m', m", J, and $R^1$ are as defined herein.

In some embodiments, the polycation is a polyamine compound. The amino groups of the polyamine can be branched (e.g., part of $R^1$) or part of the polymer backbone (e.g., part of J). The amino group can be a primary, secondary, or tertiary amino group that can be protonated to produce a cationic ammonium group at a selected pH. As discussed herein, the amino group can be further substituted with one or more suitable substituents. In particular embodiments, the amino group can be substituted with an imino group (e.g., unsubstituted or substituted guanidine). The amino group can also include quaternary ammonium group.

In general, the polyamine is a polymer with a large excess of positive charges relative to negative charges at a relevant pH, as reflected in its isoelectric point (pI), which is the pH at which the polymer has a net neutral charge. The number of amino groups present on the polycation, for example, as part of J and/or $R^1$, ultimately determines the charge of the polycation at a particular pH. For example, the polycation can have from 10 to 90 mole %, 10 to 80 mole %, 10 to 70 mole %, 10 to 60 mole %, 10 to 50 mole %, 10 to 40 mole %, 10 to 30 mole %, or 10 to 20 mole % amino groups. In some embodiments, the polyamine has an excess positive charge at a pH of about 7, with a pI significantly greater than 7.

In some embodiments, the amino group is derived from a residue of lysine, histidine, or arginine attached to the polycation, for example, through a sulfide, a sulfinyl, or a sulfonyl. Thus, in some embodiments, $R^1$ includes one or more amino groups each derived from a residue of lysine, histidine, or arginine. Any anionic counterions can be used in association with the cationic polymers. The counterions should be physically and chemically compatible with the essential components of the composition and do not otherwise unduly impair product performance, stability or aesthetics. Non-limiting examples of such counterions include halides (e.g., chloride, fluoride, bromide, iodide), sulfate and methylsulfate.

In various embodiments, the polycation comprises a biodegradable polyamine. For example, in some embodiments, J includes a biodegradable polyamine. In some embodiments, the biodegradable polyamine is a synthetic polymer or naturally-occurring polymer. The mechanism by which the polyamine can degrade will vary depending upon the polyamine that is used. In the case of natural polymers, without wishing to be bound by any particular theory, they can be biodegradable because there are enzymes that can hydrolyze the polymers and break the polymer chain. For example, proteases can hydrolyze natural proteins like gelatin. In the case of synthetic biodegradable polyamines, they can also possess chemically labile bonds. For example, β-aminoesters have hydrolyzable ester groups. In addition to the nature of the polyamine, other considerations such as the molecular weight of the polyamine and crosslink density of the adhesive can be varied in order to modify the degree of biodegradability.

In various embodiments, the biodegradable polyamine is selected from a saccharide, a peptide, a protein, a synthetic polyamine, or a combination thereof. Thus, J can include a moiety selected from a saccharide, a peptide, a protein, or a synthetic polyamine. In certain embodiments, the polyamine comprises a saccharide bearing one or more amino groups. The saccharides described herein can be monosaccharides, disaccharides, oligosaccharides, or polysaccharides. For example, the saccharides described herein have antimicrobial activity. In some embodiments, the saccharides are oligosaccharides or polysaccharides. In particular embodiments, the saccharide is chitosan or chemically modified chitosan.

In various embodiments, the polycation, for example, though J and/or $R^1$, comprises a peptide. For example, J can include a peptide moiety. In some embodiments, the polycation, for example, though J and/or $R^1$, comprises an antimicrobial peptide. For example, the antimicrobial peptide can be part of or independent from J and/or $R^1$. The peptide can be a dipeptide, a tripeptide, a tetrapeptide, an oligopeptide, or a polypeptide. In some embodiments, the peptide is an oligopeptide or a polypeptide.

In some embodiments, the polycation, for example, though J and/or $R^1$, comprises one or more polypeptide chains. The one or more polypeptide can be part of or independent from J and/or $R^1$. Thus, a person with ordinary skill in the art would appreciate that the description of polypeptide herein applies to both J and/or $R^1$ and polymer backbones that are not part of J or $R^1$.

In certain embodiments, the polycation, for example, through J and/or $R^1$, comprises one polypeptide chain. In certain embodiments, the polycation, for example, through J and/or $R^1$, comprises two polypeptide chains. In certain embodiments, the polycation, for example, through J and/or $R^1$, comprises three polypeptide chains. In certain embodiments, the polycation, for example, through J and/or $R^1$, comprises four or more polypeptide chains. In some embodiments, the polycation, for example, through J and/or $R^1$, comprises three polypeptide chains, each of which has an α-configuration. For example, the three polypeptide chains can be identical or different. In certain embodiments, the three polypeptide chains form a right-handed triple helix.

In some embodiments, each of the one or more polypeptide chains above comprises a fragment of Formula VI:

-Gly-Pro—Y—   VI wherein Y is an amino acid and Pro is proline.

In some embodiments, each of the one or more polypeptide chains above comprises a fragment of Formula VII:

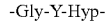
-Gly-Y-Hyp-   VII wherein Y is an amino acid and Hyp is hydroxyproline.

In certain embodiments, the polycation comprises one or more fragments each independently selected from Formula VI and Formula VII.

In various embodiments, the polycation, for example, though J and/or $R^1$, comprises an engineered protein. In some embodiments, J comprises an engineered protein. For example, the engineered protein can be produced by chemical synthesis, recombination biology, direct evolution, or combination thereof. In addition, the engineered protein can comprise one or more polypeptide chains. In some embodiments, the engineered protein comprises a single polypeptide chain. In some embodiments, the engineered protein comprises two single polypeptide chains. In some embodiments, the engineered protein comprises three single polypeptide chains.

In various embodiments, the engineered protein comprises one or more motifs each having certain biological characteristics. For example, the one or more motifs can be part of or independent from $R^1$. In some embodiments, the engineered protein comprises a motif that promotes cell interaction. For example, the engineered protein comprises a motif that promotes cell adhesion, cell migration, cell differentiation, morphogenesis, or wound healing. In particular embodiments, the engineered protein comprises a motif that promotes cell adhesion, for example, platelet adhesion, keratinocyte adhesion, or the like. In particular embodiments, the engineered protein comprises a motif that promotes cell migration, including fibroblast proliferation, chondrocyte proliferation, or other cell proliferation. In addition, the cell migration promoted by the engineered protein motif can exist in arterial wound repair, bone growth, or the like. In particular embodiments, the engineered protein comprises a motif that promotes cell differentiation, including leukocyte differentiation. In particular embodiments, the engineered protein comprises a motif that promotes morphogenesis, including branching morphogenesis, growth plate morphogenesis, mammary gland development, or the like. In certain embodiments, the engineered protein comprises a motif that promotes one or more biological functions each independently selected from fibroblast proliferation, regulation of cell proliferation, chondrocyte proliferation, platelet adhesion, keratinocyte adhesion, bone growth, response to renal injury, arterial wound repair, mast cell activation, differentiation and function of leukocytes, platelet activation, immune cell regulation, branching morphogenesis, mammary gland development, kidney function, regulation of collagen synthesis, matrix metalloproteinase (MMP) expression, innate immunity, clearance of serum glycoproteins, and collagen endocytosis.

In various embodiments, the engineered protein is a collagen, including a recombinant collagen. Thus, the recombinant collagens, described, for example, in U.S. Patent Application Publication No. 2011-0288274, the content of which is incorporated herein in its entirety, can be used here. Thus, in some embodiments, the engineered protein comprises one or more biological functioning motifs each having a sequence independently selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12. For example, the biological functioning motif can have a sequence of SEQ ID NO: 4, SEQ ID NO: 7, SEQ ID NO: 10, or SEQ ID NO: 11. In some embodiments, the engineered protein comprises one or more units each having a sequence independently selected from SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, and SEQ ID NO: 26.

In various embodiments, the engineered protein comprises a biodegradable motif. For example, the motif can be degraded in various predetermined durations.

In certain embodiments, the peptide is selected from cathelicidins, cecropins, defensins, dermcidins, histatins, magainins, melittins, protegrins, polymyxins, tachyplesins, and thionins.

In various embodiments, the polycation comprises one or more quaternary ammonium groups. The quaternary ammonium groups independently can be part of the polymer backbone, for example, as part of J, or a pendant of the polymer back bone, for example, as part of $R^1$. In some embodiments, the polycation comprises a fragment having Formula VIII or a salt thereof:

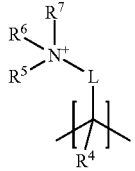

VIII wherein
L is a divalent group selected from alkyl, aryl, arylalkyl, alkoxy, and -(A)$_n$-S(O)$_x$—R$^1$—;
R$^5$, R$^6$, and R$^7$, at each occurrence, each independently is hydrogen, alkyl, alkoxy, amino, alkenyl, alkynyl, aryl, arylalkyl, cycloalkyl, or heterocyclyl;
or one of R$^5$, R$^6$, and R$^7$ is connected with the polymeric back bone to form a heterocyclyl;
or two of R$^5$, R$^6$, and R$^7$ are connected to each other to form a heterocyclyl; and
A, R$^4$, n, and x are as defined herein.
In some embodiments, the salt is a pharmaceutically acceptable salt.
In various embodiments, L is alkyl or -(A)$_n$-S(O)$_x$—R$^1$—, wherein A, R$^1$, n, and x are as defined herein. In some embodiments, L is alkyl. For example, L is methylyl, ethylyl, or propylyl. In some embodiments, L is -(A)$_n$-S(O)$_x$—R$^1$—, wherein A, R$^1$, n, and x are as defined herein. For example, the polycation has at least one fragment having Formula IX:

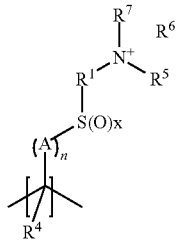

IX wherein R$^1$, R$^4$, R$^5$, R$^6$, R$^7$, A, n, and x are as defined herein.

In some embodiments, the polycation has at least one fragment having Formula Xa or Xb:

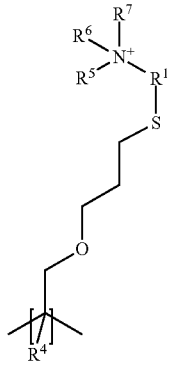

Xa

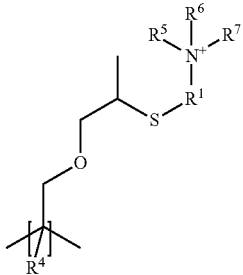

Xb wherein R$^1$, R$^4$, R$^5$, R$^6$, and R$^7$ are as defined herein.

In various embodiments, R$^5$, R$^6$, and R$^7$, at each occurrence, each is independently hydrogen, alkyl, aryl, arylalkyl, cycloalkyl, or heterocyclyl. For example, at least one of R$^5$, R$^6$, and R$^7$ is hydrogen. In some embodiments, at least one R$^5$, R$^6$, and R$^7$ at each occurrence independently is alkyl. For example, at least one R$^5$, R$^6$, and R$^7$ is methyl. In certain embodiments, R$^5$, R$^6$, and R$^7$ each is methyl.

In some embodiments, one of R$^5$, R$^6$, and R$^7$ is divalent alkyl that is connected with the polymer back bone. In certain embodiments, one of R$^5$, R$^6$, and R$^7$ is divalent methyl (methylyl) that is connected with the polymer back bone. Each of the remaining two of R$^5$, R$^6$, and R$^7$, for example, is methyl. Accordingly, the polycation can have a fragment having Formula XI:

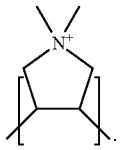

XI

In various embodiments, at least one R$^4$ is hydrogen. In various embodiments, at least one R$^4$ is methyl. In some embodiments, the polycation comprises a moiety selected from poly(diallyldimethylammonium halide), poly(vinylbenzyltrimethylammonium halide), poly(acryloxyethyltrimethylammonium halide), poly(methacryloxyethyltrimethylammonium halide), poly(methacryloxy-2-hydroxypropyltrimethylammonium halide), and a co-polymer thereof. In certain embodiments, the polycation is poly(diallyldimethylammonium chloride) (PDADMAC).

In various embodiments, the polycation comprises a polyacrylate having one or more pendant groups. For example, the backbone of the polycation, including J, can be derived from the polymerization of acrylate monomers including, but not limited to, acrylates, methacrylates, acrylamides, and the like. In some embodiments, the polycation backbone, including J, is derived from polyacrylamide. In other embodiments, the polycation, including J, is a block copolymer, where segments or portions of the copolymer possess cationic groups or neutral groups depending upon the selection of the monomers used to produce the copolymer. In some embodiments, the pendant groups of polyacrylate, including R$^1$, comprises an amino group. For example, the amino group can be a quaternary ammonium. In certain embodiments, the polycation comprises a moiety selected from poly(acryloxyethyltrimethylammonium halide), poly (methacryloxyethyltrimethylammonium halide), poly(methacryloxy-2-hydroxypropyltrimethylammonium halide), and a co-polymer thereof.

Another aspect of the present teachings relates to a polyanion comprising a polymer described herein. In various embodiments, the polyanion has a formula selected from Formulae I, II, IIIA, IIIB, IVa, and IVb.

The polyanion can comprise a synthetic polymer or naturally-occurring a polyanion. Examples of naturally-occurring polyanions include glycosaminoglycans such as condroitin sulfate, heparin, heparin sulfate, dermatan sulfate, and hyaluronic acid. In other embodiments, the acidic proteins having a net negative charge at neutral pH or proteins with a low pI can be used as naturally-occurring polyanions described herein. The anionic groups can be pendant to the polymer backbone, for example, as a part of $R^1$, and/or incorporated in the polymer backbone, for example, as a part of J.

When the polyanion is a synthetic polymer, it is generally any polymer possessing anionic groups or groups that can be readily converted to anionic groups, for example, by adjusting the pH. Examples of groups that can be converted to anionic groups include, but are not limited to, carboxylate, sulfonate, phosphonate, boronate, sulfate, borate, or phosphate. Any cationic counterions can be used in association with the anionic polymers if the considerations discussed above are met.

In various embodiments, the polyanion comprises a polycarbon, a polyether, a polyamine, a polyamide, a polyester, or a natural polymer. For example, J can be a moiety comprising polycarbon, polyether, polyamine, polyamide, polyester, or natural polymer.

In some embodiments, the polyanion, for example, though J and/or $R^1$, comprises a polyphosphate. In other embodiments, the polyanion is a polyphosphate compound having from 5 to 90 mole % phosphate groups. For example, the polyphosphate can comprise a naturally-occurring compound such as, for example, highly phosphorylated proteins like phosvitin (an egg protein), dentin (a natural tooth phosphoprotein), casein (a phosphorylated milk protein), or bone proteins (e.g., osteopontin).

Alternatively, the polyphosphate, for example, though J and/or $R^1$, can comprise a synthetic polypeptide made by polymerizing the amino acid serine and then chemically phosphorylating the polypeptide. In other embodiments, the polyphosphoserine is produced by the polymerization of phosphoserine. In some embodiments, the polyphosphate is produced by chemically or enzymatically phosphorylating a protein (e.g., natural serine- or threonine-rich proteins). In further embodiments, the polyphosphate is produced by chemically phosphorylating a polyalcohol including, but not limited to, polysaccharides such as cellulose or dextran.

In other embodiments, the polyphosphate can be a synthetic compound. For example, the polyphosphate is a polymer with pendant phosphate groups attached to the polymer backbone, for example, through $R^1$, and/or present in the polymer backbone, (e.g., a phosphodiester backbone), for example, through J.

In other embodiments, phosphorous containing polymers, for example, phospholipids, can be converted into a polyanions. For example, a phospholipid or phosphosugar can be converted into a polyanion to produce a liposome or micelle.

In some embodiments, the polyanion includes a polyacrylate having one or more pendant phosphate groups. For example, the polyanion can be derived from the polymerization of acrylate monomers including, but not limited to, acrylates, methacrylates, and the like. In certain embodiments, J is derived from the polymerization of acrylate monomers including, but not limited to, acrylates, methacrylates, and the like. In other embodiments, the polyanion is a block co-polymer, where segments or portions of the co-polymer possess anionic groups and neutral groups depending upon the selection of the monomers used to produce the co-polymer. In certain embodiments, J is such block co-polymer.

In some embodiments, J includes a polyacrylate moiety. In some embodiments, $R^1$ at each occurrence includes one or more phosphate groups.

In various embodiments, the polyanion has at least a fragment having Formula XII:

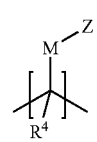

XII wherein

M at each occurrence is divalent group selected from alkyl, aryl, arylalkyl, alkoxy, and $-(A)_n-S(O)_x-R^1-$; wherein each of the alkyl, aryl, arylalkyl, and alkoxy optionally is substituted with one or more suitable substituents;

Z at each occurrence independently is an anionic group or a group that can be converted to an anionic group; and A, $R^1$, $R^4$, n, and x are as defined herein.

In various embodiments, at least one M is $-(A)_n-S(O)_x-R^1-$. For example, the polyanion has at least one fragment having Formula XIII:

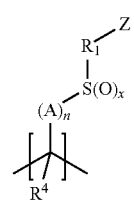

XIII wherein $R^1$, $R^4$, A, n, x, and Z are as defined herein.

In some embodiments, the polyanion has at least one fragment having Formula XIVa or XIVb:

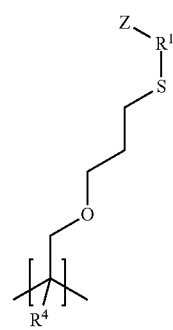

XIVa

-continued

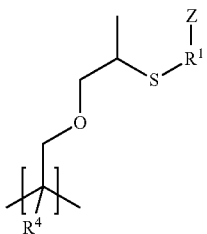

XIVb wherein $R^1$, $R^4$, and Z are as defined herein.

In various embodiments, Z is sulfate, sulfonate, carboxylate, borate, boronate, a substituted or unsubstituted phosphate, or a phosphonate. In some embodiments, Z is a phosphate.

In some embodiments, the polyanion is a polymer having at least one fragment having Formula XV:

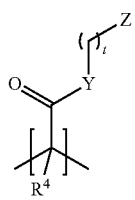

XV wherein t at each occurrence is an integer in the range of 1 and 10;
Y at each occurrence independently is oxygen, sulfur, or $NR^8$, wherein $R^8$ is hydrogen, an alkyl group, or an aryl group; and
$R^4$ and Z are as defined herein;
or a salt thereof.

In some embodiments, the salt is a pharmaceutically acceptable salt.

In some embodiments, the polyanion is a polymer having at least one fragment having Formula XVI:

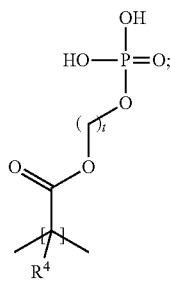

XVI wherein
$R^4$ and t are as defined herein;
or a salt thereof.

In some embodiments, the salt is a pharmaceutically acceptable salt.

In certain embodiments, at least one $R^4$ is methyl and at least one t is 2. In some embodiments, the polyanion include the copolymerization product of methacryloxyethyl phosphate and acrylamide, where the mass average molecular weight is from 10,000 to 200,000, preferably 50,000, and has phosphate groups in the amount of 20 to 90 mol %. For example, the polyanion has phosphate groups in the amount of 20 to 80 mol %, 20 to 70 mol %, 20 to 60 mol %, 20 to 50 mol %, 20 to 40 mol %, 20 to 30 mol %, 30 to 90 mol %, 40 to 90 mol %, 50 to 90 mol %, 60 to 90 mol %, 70 to 90 mol %, or 80 to 90 mol %.

Another aspect of the present teachings is an adhesive complex coacervate and their applications thereof. In general, the complex coacervates are a mixture of polycations and polyanions in balanced proportions to produce a phase separated fluid at a desired pH. In various embodiments, the adhesive complex coacervate comprises at least one polycation and at least one polyanion.

An adhesive complex coacervate is an associative liquid with a dynamic structure in which the individual polymer components can diffuse throughout the entire phase. The adhesive complex coacervates can exhibit low interfacial tension with water and hydrophilic substrates. In other words, when applied to substrates either under water or that are wet, the complex coacervate spreads evenly over the interface rather than beading up, and penetrates cracks and defects. Additionally, upon intermolecular crosslinking (or curing, discussed in detail below), the adhesive complex coacervate forms a strong, insoluble, cohesive material. Conversely, polyelectrolyte complexes (PECs), which can be a precursor to the adhesive complex coacervates described herein, are small colloidal particles.

In various embodiments, the adhesive complex coacervate, or coacervate, comprises a polycation described herein. In various embodiments, the adhesive complex coacervate, or coacervate, comprises a polyanion described herein.

Besides the polycation of the present teachings, in various embodiments, the polycation also includes a micelle or mixed micelle formed with cationic surfactants. The cationic surfactant can be mixed with nonionic surfactants to create micelles with variable charge ratios. The micelles are polycationic by virtue of the hydrophobic interactions that form a polyvalent micelle.

Examples of nonionic surfactants include the condensation products of a higher aliphatic alcohol, such as a fatty alcohol, containing about 8 to about 20 carbon atoms, in a straight or branched chain configuration, condensed with about 3 to about 100 moles, preferably about 5 to about 40 moles, most preferably about 5 to 20 moles of ethylene oxide. Examples of such nonionic ethoxylated fatty alcohol surfactants are the Tergitol™ 15-S series from Union Carbide, and Brij™ surfactants from ICI. Tergitol™ 15-S surfactants include $C_{11}$-$C_{15}$ secondary alcohol polyethyleneglycol ethers. Brij™97 surfactant is polyoxyethylene(10) oleyl ether; Brij™58 surfactant is polyoxyethylene(20) cetyl ether; and Brij™ 76 surfactant is polyoxyethylene(10) stearyl ether.

Another useful class of nonionic surfactants includes the polyethylene oxide condensates of one mole of alkyl phenol containing from about 6 to 12 carbon atoms in a straight or branched chain configuration, with ethylene oxide. Examples of nonreactive nonionic surfactants are the Igepal™ CO and CA series from Rhone-Poulenc. Igepal™ CO surfactants include nonylphenoxy poly(ethyleneoxy) ethanols. Igepal™ CA surfactants include octylphenoxy poly(ethyleneoxy)ethanols.

Another useful class of hydrocarbon nonionic surfactants includes block copolymers of ethylene oxide and propylene oxide or butylene oxide. Examples of such nonionic block copolymer surfactants are the Pluronic™ and Tetronic™ series of surfactants from BASF. Pluronic™ surfactants include ethylene oxide-propylene oxide block copolymers. Tetronic™ surfactants include ethylene oxide-propylene oxide block copolymers.

In other embodiments, the nonionic surfactants include sorbitan fatty acid esters, polyoxyethylene sorbitan fatty acid esters and polyoxyethylene stearates. Examples of such fatty acid ester nonionic surfactants are the Span™, Tween™, and Myj™ surfactants from ICI. Span™ surfactants include $C_{12}$-$C_{18}$ sorbitan monoesters. Tween™ surfactants include poly(ethylene oxide) $C_{12}$-$C_{18}$ sorbitan monoesters. Myj™ surfactants include poly(ethylene oxide) stearates.

In some embodiments, the nonionic surfactant can include polyoxyethylene alkyl ethers, polyoxyethylene alkyl-phenyl ethers, polyoxyethylene acyl esters, sorbitan fatty acid esters, polyoxyethylene alkylamines, polyoxyethylene alkylamides, polyoxyethylene lauryl ether, polyoxyethylene cetyl ether, polyoxyethylene stearyl ether, polyoxyethylene oleyl ether, polyoxyethylene octylphenyl ether, polyoxyethylene nonylphenyl ether, polyethylene glycol laurate, polyethylene glycol stearate, polyethylene glycol distearate, polyethylene glycol oleate, oxyethylene-oxypropylene block copolymer, sorbitan laurate, sorbitan stearate, sorbitan distearate, sorbitan oleate, sorbitan sesquioleate, sorbitan trioleate, polyoxyethylene sorbitan laurate, polyoxyethylene sorbitan stearate, polyoxyethylene sorbitan oleate, polyoxyethylene laurylamine, polyoxyethylene laurylamide, laurylamine acetate, hard beef tallow propylenediamine dioleate, ethoxylated tetramethyldecynediol, fluoroaliphatic polymeric ester, polyether-polysiloxane copolymer, and the like.

Examples of cationic surfactants useful for making cationic micelles include alkylamine salts, quaternary ammonium salts, sulphonium salts, and phosphonium salts. Non-limiting examples of cationic surfactants include: the quaternary ammonium surfactants, which can have up to 26 carbon atoms and include alkoxylate quaternary ammonium (AQA) surfactants as discussed in U.S. Pat. No. 6,136,769; dimethyl hydroxyethyl quaternary ammonium as discussed in U.S. Pat. No. 6,004,922; dimethyl hydroxyethyl lauryl ammonium chloride; polyamine cationic surfactants as discussed in WO 98/35002, WO 98/35003, WO 98/35004, WO 98/35005, and WO 98/35006; cationic ester surfactants as discussed in U.S. Pat. Nos. 4,228,042, 4,239,660 4,260,529 and U.S. Pat. No. 6,022,844; and amino surfactants as discussed in U.S. Pat. No. 6,221,825 and WO 00/47708, specifically amido propyldimethyl amine (APA).

Besides the polyanion of the present teachings, in some embodiments, the polyanion can be a micelle or mixed micelle formed with anionic surfactants. The anionic surfactant can be mixed with any of the nonionic surfactants described herein to create micelles with variable charge ratios. The micelles are polyanionic by virtue of the hydrophobic interactions that form a polyvalent micelle.

Other useful anionic surfactants include, but are not limited to, alkali metal and (alkyl)ammonium salts of: 1) alkyl sulfates and sulfonates such as sodium dodecyl sulfate, sodium 2-ethylhexyl sulfate, and potassium dodecanesulfonate; 2) sulfates of polyethoxylated derivatives of straight or branched chain aliphatic alcohols and carboxylic acids; 3) alkylbenzene or alkylnaphthalene sulfonates and sulfates such as sodium laurylbenzene-4-sulfonate and ethoxylated and polyethoxylated alkyl and aralkyl alcohol carboxylates; 4) glycinates such as alkyl sarcosinates and alkyl glycinates; 5) sulfosuccinates including dialkyl sulfosuccinates; 6) isothionate derivatives; 7) N-acyltaurine derivatives such as sodium N methyl-N-oleyltaurate); 8) amine oxides including alkyl and alkylamidoalkyldialkylamine oxides; and 9) alkyl phosphate mono or di-esters such as ethoxylated dodecyl alcohol phosphate ester, sodium salt. AOS-40 manufactured by Pilot Corp. can be used herein as the surfactant. In other embodiments, the surfactant is DOW-FAX 2A1 or 2G manufactured by Dow Chemical, which are alkyl diphenyl oxide disulfonates.

Representative commercial examples of suitable anionic phosphate surfactants include a mixture of mono-, di- and tri-(alkyltetraglycolether)-o-phosphoric acid esters generally referred to as trilaureth-4-phosphate commercially available under the trade designation HOSTAPHAT™ 340KL from Clariant Corp., as well as PPG-5 cetyl 10 phosphate available under the trade designation CRODAPHOS™ SG from Croda Inc., Parsipanny, N.J.

Representative commercial examples of suitable anionic amine oxide surfactants those commercially available under the trade designations AMMONYX™ LO, LMDO, and CO, which are lauryldimethylamine oxide, laurylamidopropyldimethylamine oxide, and cetyl amine oxide, all from Stepan Company.

In some aspects of the present teachings, the polycations and polyanions contain groups that permit crosslinking ("crosslinkable groups") between the two polymers upon curing to produce new covalent bonds. The mechanism of crosslinking can vary depending upon the selection of the crosslinking groups. In some embodiments, the crosslinking groups can be electrophiles and nucleophiles. For example, the polyanion can have one or more electrophilic groups, and the polycation can have one or more nucleophilic groups capable of reacting with the electrophilic groups to produce new covalent bonds; or the polycation can have one or more electrophilic groups, and the polyanion can have one or more nucleophilic groups capable of reacting with the electrophilic groups to produce new covalent bonds. Examples of electrophilic groups include, but are not limited to, anhydride groups, esters, ketones, lactams (e.g., maleimides and succinimides), lactones, epoxide groups, isocyanate groups, and aldehydes.

In some embodiments, the polycation and polyanion can crosslink with one another via a Michael addition. In certain embodiments, the crosslinking group on the polyanion comprises an olefinic group and the crosslinking group on the polycation comprises a nucleophilic group (e.g., a hydroxyl or thiol group) that reacts with the olefinic group to produce a new covalent bond. In other embodiments, the crosslinking group on the polycation comprises an olefinic group and the crosslinking group on the polyanion comprises a nucleophilic group (e.g., a hydroxyl or thiol group) that reacts with the olefinic group to produce a new covalent bond.

In other embodiments, the polycation and polyanion each have a crosslinkable group, for example, an actinically crosslinkable group. For example, at least one of $R^1$ includes a crosslinkable group. As used herein, "actinically crosslinkable group" in reference to curing or polymerizing means that the crosslinking between the polycation and polyanion is performed by actinic irradiation, such as, for example, UV irradiation, visible light irradiation, ionized radiation (e.g., gamma ray or X-ray irradiation), microwave irradiation, and the like. Actinic curing methods are well-known to a person skilled in the art. The actinically crosslinkable group can be an unsaturated organic group such as, for example, an olefinic group. Examples of olefinic groups useful herein include, but are not limited to, an acrylate group, a methacrylate group, an acrylamide group, a methacrylamide group, an allyl group, a vinyl group, a vinylester group, or a styrenyl group. In other embodiments, the actinically crosslinkable group is an azido group. For example, crosslinking can occur between the polycation and polyanion via light activated crosslinking through azido groups.

Any of the polymers described herein that can be used as the polycation and polyanion can be modified to include the actinically crosslinkable group. In some embodiments, the modification results in $R^1$ being an actinically crosslinkable group. For example, a polyphosphate can be modified to include the actinically crosslinkable group(s).

In some embodiments, the polycation and/or polyanion can include at least one fragment having Formula XVII:

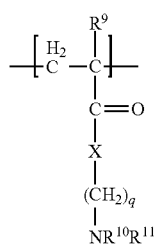

XVII wherein
$R^9$ at each occurrence is hydrogen or alkyl;
$R^{10}$, and $R^{11}$ at each occurrence independently are hydrogen, alkyl, alkenyl, alkynyl, aryl, arylalkyl, or alkoxy;
X is oxygen or $NR^{12}$, where $R^{12}$ is hydrogen or an alkyl group;
wherein at least one of $R^{10}$ or $R^{11}$ is a crosslinkable group; and
q is an integer in the range of 1 and 10,
or a salt thereof.

In some embodiments, $R^9$ is methyl. In some embodiments, $R^{10}$ is hydrogen. In some embodiments, $R^{11}$ is an acrylate or methacrylate group. In some embodiments, X is NH. In some embodiments, q is 2.

In some embodiments, the crosslinkable group is an actinically crosslinkable group.

In various embodiments, the polycation includes one or more acrylate or methacrylate groups. In some embodiments, at least one $R^1$ includes an acrylate or methacrylate. In some embodiments, the polycation is a polyamine and any of the polyamino compounds described herein that is useful as the polycation can be chemically modified to incorporate one or more acrylate or methacrylate groups. An example of this is where the branched polyamino compound has methacrylate groups attached to each arm of the polyamine. The number of acrylate or methacrylate groups attached to the polyamino compound can vary as needed.

In some embodiments, the polyanion is a phosphate compound modified to include one or more acrylate or methacrylate groups. For example, at least one $R^1$ include a phosphate. Any of the phosphate compounds described herein that is useful as the polyanion can be chemically modified to incorporate one or more acrylate or methacrylate groups. An example is where a phosphate compound with a pendant carboxylic acid group was reacted with glycidyl methacrylate to produce the phosphate compound with a terminal methacrylate group. The number of acrylate or methacrylate groups attached to the phosphate compound can vary as needed.

In other embodiments, the crosslinkable group, for example, as part of $R^1$, includes a dihydroxy-substituted aromatic group capable of undergoing oxidation in the presence of an oxidant. In some embodiments, the dihydroxy-substituted aromatic group is an ortho-dihydroxy aromatic group capable of being oxidized to the corresponding quinone. In other embodiments, the dihydroxyl-substituted aromatic group is a dihydroxyphenol or halogenated dihydroxyphenol group such as, for example, DOPA and catechol (3,4-dihydroxyphenol). For example, in the case of DOPA, it can be oxidized to dopaquinone. Dopaquinone is capable of either reacting with a neighboring DOPA group or another nucleophilic group. In the presence of an oxidant such as oxygen or other additives including, but not limited to, peroxides, periodates (e.g., $NaIO_4$), persulfates, permanganates, dichromates, transition metal oxidants (e.g., a $Fe^{+3}$ compound, osmium tetroxide), or enzymes (e.g., catechol oxidase), the dihydroxyl-substituted aromatic group can be oxidized.

In some embodiments, the polyanion comprises the polymerization product between two or more monomers, where one of the monomers has a dihydroxy aromatic group covalently attached to the monomer. For example, the polyanion can comprises the polymerization product between (1) a phosphate acrylate and/or phosphate methacrylate and (2) a second acrylate and/or second methacrylate having a dihydroxy aromatic group covalently bonded to the second acrylate or second methacrylate. In other embodiments, the polyanion comprises the polymerization product between methacryloxyethyl phosphate and dopamine methacrylamide. In each of these polymers, an acrylate containing pendant ortho-dihydroxyphenyl residue is polymerized with the appropriate monomers to produce the polyanion with pendant ortho-dihydroxyphenyl residues. Oxidation of ortho-dihydroxyphenyl groups results in orthoquinone groups, a reactive intermediate and can crosslink (i.e., react) with nucleophiles such as, for example, amino, hydroxyl, or thiol groups via a Michael-type addition to form a new covalent bond. For example, a lysyl group on the polycation can react with the orthoquinone residue on the polyanion to produce new covalent bonds. Although an ortho-dihydroxyphenyl group is a suitable crosslinking group, other groups such as, for example, tyrosine can be used herein. The importance of crosslinking with respect to the use of the complex coacervates described herein will be discussed below.

In certain embodiments, the oxidant used above can be stabilized. For example, a compound that forms a complex with periodate that is not redox active can result in a stabilized oxidant. In other words, the periodate is stabilized in a non-oxidative form and cannot oxidize the ortho-dihydroxy-substituted aromatic group while in the complex. The complex is reversible: there is a small amount of uncomplexed periodate formed. The ortho-dihydroxyl-substituted aromatic group competes with the compound for the small amount of free periodate. As the free periodate is oxidized, more is released from the equilibrium complex. In some embodiments, sugars possessing a cis,cis-1,2,3-triol grouping on a six-membered ring can form competitive periodate complexes. An example of a specific compound that forms stable periodate complex is 1,2-O-isopropylidene-alpha-D-glucofuranose (A. S. Perlin and E. von Rudloff, Canadian Journal of Chemistry. Volume 43 (1965)). The stabilized oxidant can control the rate of crosslinking. Without wishing to be bound by any particular theory, the stabilized oxidant slows the rate of oxidation providing time to add the oxidant and position the substrate before the adhesive hardens irreversibly.

In certain aspects, the coacervate also includes one or more initiators entrapped in the coacervate. Examples of initiators useful herein include a thermal initiator, a chemical initiator, or a photoinitiator. In some embodiments, when the coacervate includes a polymerizable monomer as a reinforcing component, when the initiator is activated, polymerization of the polymerizable monomer entrapped in the coacervate occurs to produce the interpenetrating network. Additionally, crosslinking can occur between the polycation and polyanion as well as with the interpenetrating network.

Examples of photoinitiators include, but are not limited to, a phosphine oxide, a peroxide group, an azide group, an α-hydroxyketone, or an α-aminoketone. In some embodiments, the photoinitiator includes, but is not limited to, camphorquinone, benzoin methyl ether, 1-hydroxycyclohexylphenyl ketone, or Darocure® or Irgacure® types, for example Darocure® 1173 or Irgacure® 2959. The photoinitiators disclosed in European Patent No. 0632329, which are incorporated by reference, can be used herein. In other embodiments, the photoinitiator is a water-soluble photoinitiator including, but not limited to, riboflavin, eosin, eosin y, and rose Bengal.

In some embodiments, the initiator has a positively charged functional group. Examples include 2,2'-azobis[2-(5-methyl-2-imidazolin-2-yl)propane]-dihydrochloride; 2,2'-azobis[2-(2-imidazolin-2-yl) propane]dihydrochloride; 2,2-azobis[2-(2-imidazo-lin-2-yl)propane]disulfate dehydrate; 2,2'-azobis(2-methylpropionamidine)dihydrochloride; 2,2'-azobis[2-(3,4,5,6-tetrahydropyrimidin-2-yl)propane]dihydrochloride; azobis(2-[1-(2-hydroxyethyl)-2-imidazolin-2-yl]propane)dihydrochloride; 2,2'-azobis(1-imino-1-pyrrolidino-2-ethylpropane)dihydrochloride and combinations thereof.

In some embodiments, the initiator is an oil soluble initiator. In particular embodiments, the oil soluble initiator includes organic peroxides or azo compounds. Examples of organic peroxides include ketone peroxides, peroxyketals, hydroperoxides, dialkyl peroxides, diacyl peroxides, peroxydicarbonates, peroxyesters, and the like. Some specific non-limiting examples of organic peroxides that can be used as the oil soluble initiator include: lauroyl peroxide, 1,1-bis(t-hexylperoxy)-3,3,5-trimethylcyclohexane, 1,1-bis(t-butylperoxy)-3,3,5-trimethylcyclohexane, t-butylperoxylaurate, t-butylperoxyisopropylmonocarbonate, t-butylperoxy-2-ethylhexylcarbonate, di-t-bulylperoxyhexahydro-terephthalate, dicumyl peroxide, 2,5-dimethyl-2,5-di(t-butylperoxy)hexane, di-t-butyl peroxide, t-bulylperoxy-2-ethylhexanoate, bis(4-t-butylcyclohexyl)peroxydicarbonate, t-amylperoxy-3,5,5-trimethylhexanoate, 1,1-di(t-amylperoxy)-3,3,5-trimethylcyclohexane, benzoyl-peroxide, t-butylperoxyacetate, and the like.

Some specific non-limiting examples of azo compounds that can be used as an oil soluble initiator include: 2,2'-azobis-isobutyronitrile, 2,2'-azobis-2,4-dimethylvaleronitrile, 1,1'-azobis-1-cyclohexane-carbonitrile, dimethyl-2,2'-azobisisobutyrate, 1,1'-azobis-(1-acetoxy-1-phenylethane), 4,4'-azobis(4-cyanopentanoic acid) and its soluble salts (e.g., sodium, potassium), and the like.

In some embodiments, the initiator is a water-soluble initiator including, but not limited to, potassium pensulfate, ammonium persulfate, sodium persulfate, and mixtures thereof. In particular embodiments, the initiator is an oxidation-reduction initiator such as the reaction product of the above-mentioned persulfates and reducing agents such as sodium metabisulfite and sodium bisulfite; and 4,4'-azobis(4-cyanopentanoic acid) and its soluble salts (e.g., sodium, potassium).

In some embodiments, multiple initiators are used, for example, to broaden the absorption profile of the initiator system in order to increase the initiation rate. For example, two different photoinitiators can be employed that are activated by different wavelengths of light. In particular embodiments, a co-initiator is used in combination with any of the initiators described herein. In some embodiments, the co-initiator is 2-(diethylamino)ethyl acrylate, 2-(dimethylamino)ethyl acrylate, 2-(dimethylamino)ethyl benzoate, 2-(dimethylamino)ethyl methacrylate, 2-ethylhexyl 4-(dimethylamino)benzoate, 3-(dimethylamino)propyl acrylate, 4,4'-bis(diethylamino)benzophenone, or 4-(diethylamino) benzophenone.

In various embodiments, the initiator and/or co-initiator are covalently attached to the polycation and/or polyanion. For example, in some embodiments, the initiator and/or co-initiator is copolymerized with monomers used to make the polycation and/or polyanion. In some embodiments, the initiators and co-initiators possess polymerizable olefinic groups such as acrylate and methacrylate groups (e.g., see examples of co-initiators above) that can be copolymerized with monomers described used to make the polycation and polyanion. In some embodiments, the initiators can be chemically grafted onto the backbone of the polycation and polyanion. Thus, in some embodiments, the photoinitiator and/or co-initiator are covalently attached to the polymer and pendant to the polymer backbone. Without attempting to limit to any particular theory, this approach will simply formulate and possibly enhance storage and stability.

In other embodiments, the crosslinkers present on the polycation and/or polyanion form coordination complexes with transition metal ions. For example, a transition metal ion can be added to a mixture of polycation and polyanion, where both polymers contain groups capable of coordinating transition metal ions. Examples of coordinating sidechains are catechols, imidazoles, phosphates, carboxylic acids, and combinations. The rate of coordination and dissociation can be controlled, for example, by the selection of the coordination group, the transition metal ion, and the pH. Thus, in addition to covalent crosslinking as described herein, crosslinking can occur through electrostatic, ionic, coordinative, or other non-covalent bonding. Transition metal ions such as, for example, iron, copper, vanadium, zinc, and nickel can be used herein.

Another aspect of the present teachings relates methods for preparing polymers, polycations, and polyanions described herein. Without attempting to limit the scope of the present teachings, synthetic approaches of the present teachings can introduce functionalities to polymers.

In various embodiments, the method comprises providing a polymer having a vinyl group (i.e., having a carbon-carbon double bond) or a ethynyl group (i.e., having a carbon-carbon triple bond) and transforming the vinyl group or the ethynyl group.

The transformation can be a radical reaction, a nucleophilic reaction, or an electrophilic reaction. In some embodiments, the transforming step comprises forming one or more carbon-heteroatom bonds. In certain embodiments, the transforming step comprises forming one carbon-heteroatom bonds. In certain embodiments, the transforming step comprises forming two or more carbon-heteroatom bonds. The heteroatom can be O, N, or S. In certain embodiments, the heteroatom is N or S. In particular embodiments, the heteroatom is N. In particular embodiments, the heteroatom is S.

The polymers having a vinyl or ethynyl group can be any polymers. For example, the polymers can have a vinyl group. Thus, in various embodiments, the method is illustrated as:

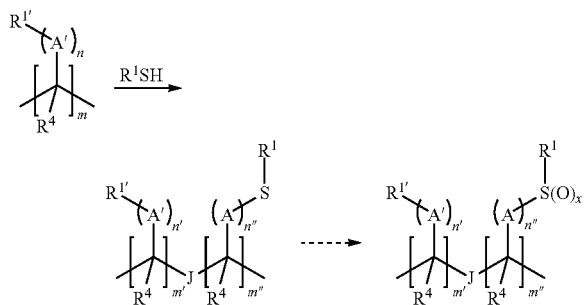

wherein m'+m"=m; and
A, A', J, $R^1$, $R^{1'}$, $R^4$, n, n', n", and x are as defined herein.

In various embodiments, where the polymer before transformation is pAGE, the vinyl side group is transformed with a nucleophile under mild conditions.

For example, the nucleophile can be a thiol and other sulfide salts, such as thiolates, thiocarboxylic acids, dithiocarbonates, and dithiocarbamates. Further, the nucleophile can be a nitrogen-containing compound, such as an azide, amine or nitrite. Thus, in certain embodiments, the method comprises providing pAGE and transforming a vinyl group in pAGE to produce a sulfide. For example, the method can have the following general reaction scheme:

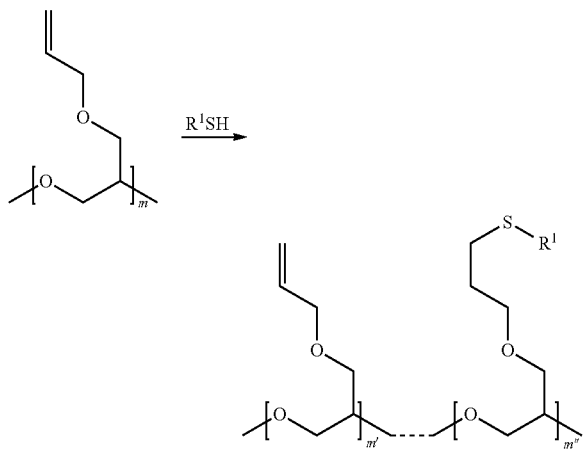

wherein m'+m"=m; and $R^1$ is as defined herein.

As discussed here, at least one $R^1$ can include a cationic moiety, an anionic moiety, or a crosslinkable group.

Another aspect of the present teachings is synthesis of an adhesive complex coacervate. The synthesis described herein can be performed using a number of techniques and procedures. Exemplary techniques for producing the coacervates with the polymerizable monomer are provided in the Examples. In some embodiments, an aqueous solution of polycation is mixed with an aqueous solution of polyanion, where one or both of the solutions may contain a polymerizable monomer and other optional components (e.g., fillers, initiators, etc.). In some embodiments, the pH of each solution is adjusted to a desired pH (e.g., physiological pH) prior to mixing with one another to produce a complex coacervate. Alternatively, in certain embodiments, after mixing the polycation, polyanion, polymerizable monomer, and optional components, the pH of the resulting solution is adjusted to produce a complex coacervate. Upon mixing, the adhesive complex coacervate forms as a separate phase that may be used to produce the adhesive.

In some embodiments, adhesive complex coacervate as described herein is cured to induce crosslinking within the coacervate to produce a cured adhesive complex coacervate. In various embodiments, the cured adhesive complex coacervate is referred to herein as "an adhesive". Without limiting the scope of the present teaching to certain theory or hypothesis, depending upon the selection of starting materials, varying degrees of crosslinking can occur throughout the coacervate during curing. In some embodiments, polycations and polyanions as described herein are crosslinked with one another by covalent bonds upon curing. In other embodiments, the polycations and/or polyanions as described herein are crosslinked with a reinforcing component.

In various embodiments, after the adhesive complex coacervate has been produced and applied to a substrate or adherend, it is converted to a load bearing adhesive bond. In some embodiments, the adhesive is produced by a process comprising (a) providing an adhesive complex coacervate described herein, wherein the adhesive complex coacervate comprises a polymerizable monomer, and (b) curing the adhesive complex coacervate to produce an interpenetrating network.

In the above embodiments, without limiting the present teachings to any particular theory, step (b) involves curing the adhesive complex coacervate to polymerize the polymerizable monomer and produce an interpenetrating network throughout the coacervate. In some embodiments, the polycations and polyanions are crosslinked with one another by covalent bonds upon curing. In some embodiments, the polycations and/or polyanions are crosslinked with the interpenetrating network. For example, the polymerizable monomer can possess groups that can covalently crosslink with the polycation and/or polyanion, which enhances the overall mechanical properties of the coacervate. In certain embodiments, adhesive complex coacervates as described herein have enhanced mechanical properties.

Without limiting the scope of the present teachings to any particular theory, polymerizing the polymerizable monomer to produce the interpenetrating network can vary depending upon the nature of the polymerizable monomer. For example, if the polymerizable monomer has one or more polymerizable olefinic groups, an initiator and a co-initiator can be incorporated into the coacervate using the method described herein, and the coacervate can be exposed to light. In certain embodiments, the polymerizable monomer polymerizes in the coacervate to produce an interpenetrating network. Any of the initiators and co-initiators described herein can be used herein.

In certain aspects, when the polycation and polyanion possess orthogonally crosslinkable groups, the groups can be crosslinked with one another prior to the polymerization of the polymerizable monomer, after the polymerization of the polymerizable monomer, or simultaneously with the polymerization of the polymerizable monomer. For example, using the techniques described herein and in the Examples, the coacervate can be contacted with an oxidant such as $O_2$, $NaIO_4$, a peroxide, or a transition metal oxidant in order to facilitate crosslinking. As discussed above, without limiting the scope of the present teachings to any particular theory, the rate of oxidative crosslinking can be controlled when the oxidant is combined with certain sugars. In certain embodiments, crosslinking of complex coacervates as described herein is delayed. In certain embodiments, crosslinking of complex coacervates as described herein is accelerated. In certain embodiments, crosslinking of complex coacervates as described herein is performed in a stage-wise manner.

As discussed above, the polycation and/or polyanion can be covalently attached to the interpenetrating network. In some embodiments, the polycation and/or polyanion as described herein include olefinic groups capable of polymerizing with the polymerizable monomer to form a covalent bond with the interpenetrating network. In some embodiments, the polycation and/or polyanion include nucleophilic groups (e.g., thiols or amines) capable of reacting with groups on the interpenetrating network (e.g., olefinic groups).

In other aspects, when the reinforcing component is a filler, the filler can be functionalized such that it can form covalent or non-covalent bonds with the polycation, polyanion, and/or interpenetrating network. For example, if the filler is functionalized with olefinic groups such as acrylate groups, it can polymerize with the polymerizable monomer such that the filler is covalently bonded to the resulting interpenetrating network. Alternatively, in some embodiments, the filler is modified with nucleophilic groups capable of reacting with electrophilic groups on the polycation, polyanion, and/or interpenetrating network. In some embodiments, the filler possesses groups that permit electrostatic interactions between the polycation, polyanion, interpenetrating network, or any combination thereof.

In general, the interpenetrating polymer network should be biodegradable and biocompatible for medical applications. Thus, in some embodiments, the polymerizable monomer is selected such that a biodegradable and biocompatible interpenetrating polymer network is produced upon polymerization. For example, the polymerizable monomer can possess cleavable ester linkages. In particular embodiments, the polymerizable monomer is hydroxypropyl methacrylate (HPMA). In some embodiments, biodegradable crosslinkers are used to polymerize biocompatible water-soluble monomers such as, for example, alkyl methacrylamides. The crosslinker could be enzymatically degradable, like a peptide, or chemically degradable by having an ester or disulfide linkage.

The adhesive complex coacervates described herein have several desirable features. For example, the adhesive complex coacervates can be phase separated from water although being water-borne and/or have low interfacial tension with water and wettable substrates. Thus, in some embodiments, the adhesive complex coacervates are delivered underwater without dispersing into the water. In some embodiments, the adhesive complex coacervates spread over the interface rather than beading up when applied to a wet substrate. In certain embodiments, the adhesive complex coacervates are effective in bonding two adherends together, particularly when the adherends are wet or will be exposed to an aqueous environment. Without attempting to limit to any particular theory, the formation of the interpenetrating network enhances the mechanical properties of the coacervate including, but not limited to, cohesion (i.e., internal strength), fracture toughness, extensibility, fatigue resistance, elastic modulus, etc. In other words, upon formation of the interpenetrating network, the strength of the bond between the two adherends formed by the coacervate is increased significantly. The degree of crosslinking that occurs during the curing step can vary depending upon the selection of starting materials.

Another aspect of the present teachings relate to kits for making adhesive complex coacervates described herein. In some embodiments, the kit comprises (1) a complex coacervate mixture comprising a polycation and a polyanion and (2) an initiator and optional coinitiator. In some embodiments, the kit comprises a complex coacervate mixture comprising a polycation and a polyanion where an initiator and optional coinitiator are covalently attached to the polycation and/or polyanion. In some embodiments, the kit comprises (1) a complex coacervate mixture comprising a polycation and a polyanion, (2) a polymerizable monomer, and (3) an initiator and optional coinitiator. In some embodiments, the kit comprises (1) a complex coacervate mixture comprising a polycation and a polyanion wherein an initiator and optional coinitiator are covalently attached to the polycation and/or polyanion and (2) a polymerizable monomer. In some embodiments, the kit comprises (1) a complex coacervate mixture comprising a polycation and a polyanion, (2) a polymerizable monomer, (3) a filler, and (4) an initiator and optional coinitiator. In some embodiments, the kit comprises (1) a complex coacervate mixture comprising a polycation and a polyanion wherein an initiator and optional coinitiator are covalently attached to the polycation and/or polyanion, (2) a polymerizable monomer, and (3) a filler. In some embodiments, the kit comprises (1) a complex coacervate mixture comprising a polycation and a polyanion, (2) a filler, and (3) an initiator and optional coinitiator. In some embodiments, the kit comprises (1) a complex coacervate mixture comprising a polycation and a polyanion wherein an initiator and optional coinitiator are covalently attached to the polycation and/or polyanion and (2) a filler. The kits can include additional components, including an oxidant as described herein.

The adhesive complex coacervates described herein have numerous benefits with respect to their use as biological glues and delivery devices. For example, the coacervates can have low initial viscosity, can have specific gravity greater than one, and can contain a significant fraction of water by weight, can have a low interfacial tension in an aqueous environment, all of which may contribute to their ability to adhere to a wet surface. Without limiting the scope of the present teachings to any particular theory, adhesive complex coacervates of the present teachings are water-borne, eliminating the need for potentially toxic solvents. In some embodiments, despite being water-borne, they are phase separated from water. This may allow the adhesive complex coacervate to be delivered underwater without dispersing. In some embodiments, the adhesive complex coacervates of the present teachings are dimensionally stable after crosslinking so that when applied in a wet physiological environment, they do not swell. Without being limited to any particular theory, the lack of swelling, i.e., absorption of water, is due to the phase-separated nature of the copolymer network. In various embodiments, the dimensional stability of a cured adhesive complex coacervate is of critical importance for medical adhesives; swelling after application can damage surrounding tissues and/or cause pain. In some embodiments, dimensional stability is a major advantage over tissue adhesives/sealants based on crosslinked PEG hydrogels. In some embodiments, an additional advantage with respect to the bonding mechanism (i.e., crosslinking) of the adhesive complex coacervates includes low heat production during setting, which prevents damage to living tissues.

The adhesive complex coacervates described herein can be applied to a number of different biological substrates. The substrate can be contacted in vitro or in vivo. The rate of curing can be modified accordingly based upon the type and amount of initiator used and/or the amount of crosslinking groups. In the case when the polyanion and polycation are capable of crosslinking with one another, the rate of crosslinking can be controlled, for example, by pH and the presence of an oxidant or other agents that facilitate crosslinking.

In various embodiments, the adhesive complex coacervate described herein has antimicrobial activity. Thus, adhesive complex coacervates of the present teachings can be used to prevent or treat infection caused by bacteria, fungi, yeast, or protozoan. In some embodiments, the adhesive complex coacervate is applied to an infection of a subject in need thereof. In some embodiments, the adhesive complex coacervate is part of wound dressing. In certain embodiments, the infection occurs in epidermis, dermis, or hypodermis. Accordingly, in some embodiments, the adhesive complex coacervate is used topically. In certain embodiments, the infection occurs in muscle and related tissues (e.g., muscle, ligaments, tendons). In certain embodiments, the infection occurs in certain body cavities. For example, the infection occurs in the thoracic cavity, abdominal cavity, pelvic cavity, cranial cavity, or spinal cavity. In certain embodiments, the infection occurs in certain internal organs. For example, the infection occurs in stomach, intestines, bronchi, lung, bladder, blood vessels, heart, ovaries, fallopian tubes, uterus, vagina, and cartilage. Accordingly, in some embodiments, the adhesive complex coacervate is used internally.

The adhesive complex coacervate as described herein can be used in a variety of surgical procedures. In some embodiments, the adhesive complex coacervates is used to treat ocular wounds caused by trauma or by the surgical procedures. In some embodiments, the adhesive complex coacervate is used to repair a corneal or schleral laceration in a subject. In other embodiments, adhesive complex coacervate is used to facilitate healing of ocular tissue damaged from a surgical procedure (e.g., glaucoma surgery or a corneal transplant). The methods disclosed in U.S. Published Application No. 2007/0196454, which are incorporated by reference, can be used to apply the coacervates described herein to different regions of the eye.

In other embodiments, the adhesive complex coacervate as described herein is used to inhibit blood flow in a blood vessel of a subject. In some embodiments, the adhesive complex coacervate is injected into the vessel followed by polymerizing the polymerizable monomer as described herein to partially or completely block the vessel. This method has numerous applications including hemostasis or the creation of an artificial embolism to inhibit blood flow to a tumor or aneurysm or other vascular defect.

In some embodiments, the adhesive complex coacervate as described herein is used to seal the junction between skin and an inserted medical device such as catheters, electrode leads, needles, cannulae, osseo-integrated prosthetics, and the like. In certain embodiments, the adhesive complex coacervate prevents infection at the entry site when the device is inserted in the subject. In other embodiments, the adhesive complex coacervate is applied to the entry site of the skin after the device has been removed in order to expedite wound healing and prevent further infection.

In other embodiments, the adhesive complex coacervate as described herein is used to close or seal a puncture in an internal tissue or membrane. Alternatively, in some embodiments, the adhesive complex coacervate is applied to the puncture or incision to seal the puncture and expedite the healing and prevent further infection.

In various embodiments, the adhesive complex coacervate as described herein is used for anastomosis. In some embodiments, the adhesive complex coacervate is used to connect/reconnect two or more blood vessels, two or more segments in the gastrointestinal tract, two or more segments in the urinary tract, two nerve tissues, two segments in the fallopian tube, or two segments in the vas deferens. In some embodiments, the adhesive complex coacervate is used as anastomosis and to expedite the healing and prevent further infection.

In various embodiments, the adhesive complex coacervate as described herein is used to repair a number of different bone fractures and breaks. Without limiting to any particular theory, it is believed that the adhesive complex coacervate adheres to bone (and other minerals) through several mechanisms. The surface of the bone's hydroxyapatite mineral phase $(Ca_5(PO_4)_3(OH))$ is an array of both positive and negative charges. The negative groups present on the polyanion (e.g., phosphate groups) can interact directly with the positive surface charges or it can be bridged to the negative surface charges through the cationic groups on the polycation and/or multivalent cations. Likewise, direct interaction of the polycation with the negative surface charges can contribute to adhesion. Additionally, when the polycation and/or polyanion contain catechol moieties, they can facilitate the adhesion of the adhesive complex coacervate to readily wet hydroxyapatite. Other adhesion mechanisms include direct bonding of unoxidized crosslinker (e.g., ortho-dihydroxyphenyl compounds or other catechols) to hydroxyapatite. Alternatively, oxidized crosslinkers can couple to nucleophilic sidechains of bone matrix proteins.

Examples of such breaks include a complete fracture, an incomplete fracture, a linear fracture, a transverse fracture, an oblique fracture, a compression fracture, a spiral fracture, a comminuted fracture, a compacted fracture, or an open fracture. In some embodiments, the fracture is an intra-articular fracture or a craniofacial bone fracture. Fractures such as intra-articular fractures are bony injuries that extend into and fragment the cartilage surface. In some embodiments, the adhesive complex coacervate aids in the maintenance of the reduction of such fractures, allows for less invasive surgery, reduces operating room time, reduces costs, and provides a better outcome by reducing the risk of post-traumatic arthritis.

In other embodiments, the adhesive complex coacervate is used to join small fragments of highly comminuted fractures. In certain embodiments, small pieces of fractured bone is adhered to an existing bone. In some embodiments, without limiting to any particular theory, the adhesive complex coacervate is injected in small volumes to create spot welds as described herein in order to fix the fracture rather than filling the entire crack followed by curing the complex coacervate. The small biocompatible spot welds would minimize interference with healing of the surrounding tissue and would not necessarily have to be biodegradable. In this respect, it would be similar to permanently implanted hardware.

Another aspect of the present teachings is using the adhesive complex coacervate as described herein to secure a patch to bone and other tissues such as, for example, cartilage, ligaments, tendons, soft tissues, organs, and synthetic derivatives of these materials. In various embodiments, the patch is a tissue scaffold or other synthetic materials or substrates typically used in wound healing applications.

In various embodiments, the adhesive complex coacervate as described herein has numerous dental applications. In some embodiments, the adhesive complex coacervate is used to seal breaks or cracks in teeth, for securing crowns, or allografts, or seating implants and dentures. In some embodiments, the adhesive complex coacervate is applied to a specific point in the mouth (e.g., jaw, sections of a tooth) followed by attaching the implant to the substrate and subsequent curing.

In other embodiments, the adhesive complex coacervate adheres a substrate to a tissue. In some embodiments, the adhesive complex coacervate is applied to the metal substrate, the tissue, or both prior to adhering the substrate to the tissue. In certain embodiments, the crosslinking group present on the polycation and/or polyanion form a strong bond with the implant. In particular embodiments, the adhesive complex coacervate is used to bond a substrate to bone. In some embodiments, the substrate is made of titanium oxide, stainless steel, or other metals commonly used to repair fractured bones. In other embodiments, the substrate is a fabric (e.g., an internal bandage), a tissue graft, or a wound healing material. Alternatively, in some embodiments, the adhesive complex coacervate is used to adhere a scaffold or patch to the tissue or membrane.

In some embodiments, the adhesive complex coacervate as described herein is used in tissue engineering in vitro or in vivo. In particular embodiments, the adhesive complex coacervate is used to make a structure, for example, by a known process. In certain embodiments, the known process is selected from injection molding, extrusion, compressing molding, transfer molding, laminating, vacuum forming, and rotational molding. In certain embodiments, the known process is a rapid prototyping process. The rapid prototyping process can be stereolithography, laminated object manufacturing, or three dimensional (3-D) printing. The structure obtained from the above process can be further modified for its application.

In various embodiments, the structure is a scaffold. In some embodiments, the structure allows or facilitates cell attachment, cell adhesion, cell differentiation, cell morphogenesis, protein binding, or wound healing. In certain embodiments, the structure promotes cell attachment, cell adhesion, cell differentiation, cell morphogenesis, or protein binding. In particular embodiments, the structure promotes cell attachment. In particular embodiments, the structure promotes cell adhesion, for example, platelet adhesion, keratinocyte adhesion, or the like. In particular embodiments, the structure promotes cell migration, including fibroblast proliferation, chondrocyte proliferation, or other cell proliferation. In addition, the cell migration promoted by the structure can exist in arterial wound repair, bone growth, or the like. In particular embodiments, the structure promotes cell differentiation, including leukocyte differentiation. In particular embodiments, the structure promotes morphogenesis, including branching morphogenesis, growth plate morphogenesis, mammary gland development, or the like. In particular embodiments, the structure promotes protein binding. In some embodiments, the structure promotes one or more biological functions each independently selected from fibroblast proliferation, regulation of cell proliferation, chondrocyte proliferation, platelet adhesion, keratinocyte adhesion, bone growth, response to renal injury, arterial wound repair, mast cell activation, differentiation and function of leukocytes, platelet activation, immune cell regulation, branching, morphogenesis, mammary gland development, kidney function, regulation of collagen synthesis, matrix metalloproteinase (MMP) expression, innate immunity, clearance of serum glycoproteins, and collagen endocytosis.

In certain embodiments, the structure is implantable. In certain embodiments, the structure is biodegradable.

Another aspect of the present teachings is using the adhesive complex coacervate as described herein to encapsulate one or more bioactive agents. The bioactive agents can be any drug including, but not limited to, antibiotics, pain relievers, immune modulators, growth factors, enzyme inhibitors, hormones, mediators, messenger molecules, cell signaling molecules, receptor agonists, or receptor antagonists.

In various embodiments, the bioactive agent is a nucleic acid. The nucleic acid can be an oligonucleotide, deoxyribonucleic acid (DNA), ribonucleic acid (RNA), or peptide nucleic acid (PNA). The nucleic acid of interest can be nucleic acid from any source, such as a nucleic acid obtained from cells in which it occurs in nature, recombinantly produced nucleic acid, or chemically synthesized nucleic acid. For example, the nucleic acid can be cDNA or genomic DNA or DNA synthesized to have the nucleotide sequence corresponding to that of naturally-occurring DNA. The nucleic acid can also be a mutated or altered form of nucleic acid (e.g., DNA that differs from a naturally occurring DNA by an alteration, deletion, substitution or addition of at least one nucleic acid residue) or nucleic acid that does not occur in nature.

In various embodiments, the bioactive agent is used in bone treatment applications. For example, in some embodiments, the bioactive agent can be bone morphogenetic proteins (BMPs) and prostaglandins. When the bioactive agent is used to treat osteoporosis, bioactive agents known in the art such as, for example, bisphosphonates, can be delivered locally to the subject by the adhesive complex coacervate described herein.

In certain aspects, the filler used to produce the coacervate also possesses bioactive properties. For example, in some embodiments, when the filler is a silver particle, the particle can also behave as an anti-bacterial agent. The rate of release can be controlled by the selection of the materials used to prepare the complex as well as the charge of the bioactive agent if the agent is a salt. Thus, in some embodiments, the insoluble solid can perform as a localized controlled drug release depot. It may be possible to simultaneously fix tissue and bones as well as deliver bioactive agents to provide greater patient comfort, accelerate bone healing, and/or prevent infections.

The following examples are put forth so as to assist those of ordinary skill in the art in understanding the present teachings, including the claims, and are intended to be purely exemplary and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Preparation of of poly(t-butyl glcidyl ether).

Solutions of 0.00426 mole of 3-phenyl-1-propanol and 0.000425 mole of potassium t-butoxide were added to 15.0 mL of diglyme in a 100 mL round bottom under dry conditions. The mixture was stirred for 30 minutes at room temperature, after which t-butanol was distilled off for one hour at 40° C. The mixture was cooled to room temperature and 0.0849 mole t-butyl glycidyl ether added to the flask to make a final concentration of 20.0 M. The flask was placed in an oil bath at 120° C. for 21 hours. The reaction mixture was cooled to room temperature, then vacuum distilled at 80° C. for one hour. The polymer was dissolved in methylene chloride, and the solution was washed with 100 mL deionized water and 5% NaCl solution. The organic phase was collected and distilled to remove excess solvent. The polymer yield is greater than 95%.

The composition of the polymer was determined by 1H-NMR. The $M_n$ value was 30.4 as determined by end-group analysis.

Poly(allyl glycidyl ether) (pAGE) can be prepared by using a similar method. The monomer allyl glycidyl ether is used. To protect the vinyl side groups, the polyethers are treated with trifluoracetic acid to yield the alcohol pendent group. The polyol is derivatized with a vinyl group by reaction with glycidyl methacrylate in the presence of a strong base such as NaOH.

To functionalize the polymer to form a polycation or a polyanion, thiol-ene chemistry is used. The vinyl-containing polymer is reacted with an appropriate thiolated group under mild conditions. For example, pAGE is reacted with thiol-containing polyamine to form an amine-containing polycation or is reacted with thiol-containing polyphosphate to form a phosphate-containing polyanion.

The adhesive coacervate is formed by crosslinking a mixture comprising of polycations and polyanions. For example, amine-containing polycations and phosphate-containing polyanions are dissolved in a solution of polymerizable monomer polyethylene glycol (PEG) diacrylate. The pH of the solution is adjusted to a desired pH while stirring. The coacervate phase settles to the bottom with a clear supernatant at the top. The supernatant is then removed from the top of the settled coacervate phase.

The vinyl-functionalized polymer can react with a thiol-modified substrate, or other appropriate nucleophile, to create a crosslinked network. In various embodiments, the nucleophilic group can be present on the exposed surfaces of tissues. In other embodiments, the nucleophilic group is a free thiol or a primary amine group. In some embodiments, the nucleophile is present on a di-functional or multi-functional substrate mixed with the vinyl-functionalized polymer. In some embodiments, the functional substrate is a multi-functional small molecule, or a polymer such as a linear, co- or branched-polymer, or a surface functionalized particle, such as a microparticle or a nanoparticle.

Without limiting the present teachings to any particular theory, the surface of the bone's hydroxyapatite mineral phase ($Ca_5(PO_4)_3(OH)$) is an array of both positive and negative charges. The negative groups in the functionalized polycation, such phosphate groups, can interact directly with the positive surface charges or be bridged to the negative surface charges through the cationic groups on the polycation and/or multivalent cations. Likewise, direct interaction of the polymer with the negative surface charges would contribute to adhesion. Additionally, when the polycation and/or polyanion contain catechol moieties, they can facilitate the adhesion of the coacervate to readily wet hydroxyapatite. Other adhesion mechanisms include direct bonding of unoxidized crosslinker (e.g., ortho-dihydroxyphenyl compounds or other catechols) to hydroxyapatite. Alternatively, oxidized crosslinkers can couple to nucleophilic sidechains of bone matrix proteins.

Various modifications and variations can be made to the compounds, compositions, and methods described herein. Other aspects of the compounds, compositions and methods described herein will be apparent from consideration of the specification and practice of the compounds, compositions and methods disclosed herein. It is intended that the specification and examples be considered as exemplary.

What is claimed is:

1. A coacervate comprising a polycation and a polyanion, wherein the polycation and/or the polyanion comprises a moiety of Formula II:

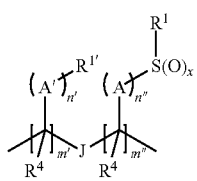

wherein
A at each occurrence is O, $NR^2$, or $C(R^3)_2$;
A' at each occurrence is O, $NR^2$, $C(R^3)_2$ or $CR^3$;
$R^1$ and $R^2$ at each occurrence independently is hydrogen, alkyl, alkenyl, aryl, arylalkyl, cycloalkyl, heteroaryl, or heterocyclyl, wherein each of the alkyl, alkenyl, aryl, arylalkyl, cycloalkyl, heteroaryl, and heterocyclyl optionally is substituted with one or more substituents selected from the group consisting of alkyl, alkenyl, alkynyl, aryl, heteroaryl, cycloalkyl, heterocyclyl, heteroaryl, alkoxy, aryloxy, cyano, hydroxyl, oxo, imino, halo, amino, phosphate, phosphonate, sulfate, sulfonate and borate;
$R^{1'}$ at each occurrence is hydrogen, alkyl, alkenyl, aryl, arylalkyl, cycloalkyl, heteroaryl, or heterocyclyl, wherein each of the alkyl, alkenyl, aryl, arylalkyl, cycloalkyl, heteroaryl, and heterocyclyl optionally is substituted with one or more substituents selected from the group consisting of alkyl, alkenyl, alkynyl, aryl, heteroaryl, cycloalkyl, heterocyclyl, heteroaryl, alkoxy, aryloxy, cyano, hydroxyl, oxo, imino, halo, amino, phosphate, phosphonate, sulfate, sulfonate and borate, wherein at least one $R^{1'}$ comprises a vinyl or ethynyl group;
$R^3$ at each occurrence is hydrogen, alkyl, alkenyl, aryl, arylalkyl, cycloalkyl, heteroaryl, heterocyclyl, hydroxyl, alkoxyl, aroxyl, ester, sulfide, sulfinyl, sulfonyl, halo, cyano, nitro, carbonyl, or carboxylate, wherein each of the alkyl, alkenyl, aryl, arylalkyl, cycloalkyl, heteroaryl, heterocyclyl, alkoxyl, aroxyl, ester, sulfide, sulfinyl, sulfonyl, carbonyl, and carboxylate optionally is substituted with one or more substituents selected from the group consisting of alkyl, alkenyl, alkynyl, aryl, heteroaryl, cycloalkyl, heterocyclyl, heteroaryl, alkoxy, aryloxy, cyano, hydroxyl, oxo, imino, halo, amino, phosphate, phosphonate, sulfate, sulfonate and borate; or
two $R^3$ groups are combined to form oxo or imino;
$R^4$ at each occurrence is hydrogen or alkyl;
x is 0, 1, or 2;
m', m", n', and n" at each occurrence is an integer; and
J represents other parts of the polycation or polyanion.

2. The coacervate of claim 1, wherein A at each occurrence is O or $C(R^3)_2$.

3. The coacervate of claim 1, wherein at least one A is $C(R^3)_2$, wherein $R^3$ is hydrogen or optionally substituted alkyl.

4. The coacervate of claim 1, wherein at least one A' is oxygen.

5. The coacervate of claim 1, wherein the moiety of Formula II is of Formula IIIa or Formula IIIb:

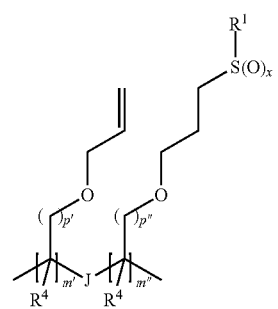

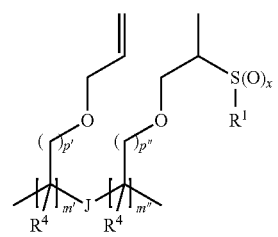

wherein p' and p" each at each occurrence is an integer.

6. The coacervate of claim 1, wherein the polycation comprises the moiety of Formula II.

7. The coacervate of claim 6, wherein the polycation comprises one or more amino groups.

8. The coacervate of claim 6, wherein the polycation comprises a peptide or an engineering protein.

9. The coacervate of claim 1, wherein the polyanion comprises the moiety of Formula II.

10. The coacervate of claim 9, wherein the polyanion comprises a sulfate, a sulfonate, a carboxylate, a borate, a boronate, a phosphonate, or a phosphate group.

11. The coacervate of claim 1, wherein the polycation and/or the polyanion is cross-linked.

12. The coacervate of claim 1, wherein the coacervate is an adhesive complex coacervate.

* * * * *

SEQUENCE LISTING

```
<160> NUMBER OF SEQ ID NOS: 26

<210> SEQ ID NO 1
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is a hydroxyproline

<400> SEQUENCE: 1

Gly Phe Xaa Gly Glu Arg
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
```

```
<223> OTHER INFORMATION: Xaa is a hydroxyproline

<400> SEQUENCE: 2

Gly Leu Xaa Gly Glu Arg
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide

<400> SEQUENCE: 3

Gly Ala Ser Gly Glu Arg
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

Gly Leu Pro Gly Glu Arg
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Gly Leu Pro Gly Glu Asn
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide

<400> SEQUENCE: 6

Gly Leu Pro Gly Glu Lys
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7

Gly Arg Pro Gly Glu Arg
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide
```

<400> SEQUENCE: 8

Gly Arg Pro Gly Glu Asn
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic peptide

<400> SEQUENCE: 9

Gly Arg Pro Gly Glu Lys
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide

<400> SEQUENCE: 10

Gly Phe Pro Gly Glu Arg
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic peptide

<400> SEQUENCE: 11

Gly Phe Pro Gly Glu Asn
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide

<400> SEQUENCE: 12

Gly Phe Pro Gly Glu Lys
1               5

<210> SEQ ID NO 13
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Leu, Arg or Phe
<220> FEATURE:
<221> NAME/KEY: MISC_FEATURE
<222> LOCATION: (6)..(6)
<223> OTHER INFORMATION: Xaa is Pro
<220> FEATURE:
<221> NAME/KEY: MISC_FEATURE

```
<222> LOCATION: (8)..(8)
<223> OTHER INFORMATION: Xaa is Glu
<220> FEATURE:
<221> NAME/KEY: MISC_FEATURE
<222> LOCATION: (9)..(9)
<223> OTHER INFORMATION: Xaa is Arg, Lys or Asn
<220> FEATURE:
<221> NAME/KEY: MISC_FEATURE
<222> LOCATION: (11)..(12)
<223> OTHER INFORMATION: Xaa is any amino acid

<400> SEQUENCE: 13

Gly Xaa Xaa Gly Xaa Xaa Gly Xaa Xaa Gly Xaa Xaa
 1               5                  10

<210> SEQ ID NO 14
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid

<400> SEQUENCE: 14

Gly Xaa Xaa Gly Leu Pro Gly Glu Arg Gly Xaa Xaa
 1               5                  10

<210> SEQ ID NO 15
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid

<400> SEQUENCE: 15

Gly Xaa Xaa Gly Leu Pro Gly Glu Asn Gly Xaa Xaa
 1               5                  10

<210> SEQ ID NO 16
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid

<400> SEQUENCE: 16

Gly Xaa Xaa Gly Leu Pro Gly Glu Lys Gly Xaa Xaa
 1               5                  10
```

<210> SEQ ID NO 17
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid

<400> SEQUENCE: 17

Gly Xaa Xaa Gly Arg Pro Gly Glu Arg Gly Xaa Xaa
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid

<400> SEQUENCE: 18

Gly Xaa Xaa Gly Arg Pro Gly Glu Asn Gly Xaa Xaa
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid

<400> SEQUENCE: 19

Gly Xaa Xaa Gly Arg Pro Gly Glu Lys Gly Xaa Xaa
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid

<400> SEQUENCE: 20

Gly Xaa Xaa Gly Phe Pro Gly Glu Arg Gly Xaa Xaa
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid

<400> SEQUENCE: 21

Gly Xaa Xaa Gly Phe Pro Gly Glu Asn Gly Xaa Xaa
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid

<400> SEQUENCE: 22

Gly Xaa Xaa Gly Phe Pro Gly Glu Lys Gly Xaa Xaa
1               5                   10

<210> SEQ ID NO 23
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is Lau, Arg or Phe
<220> FEATURE:
<221> NAME/KEY: MISC_FEATURE
<222> LOCATION: (3)..(3)
<223> OTHER INFORMATION: Xaa is Pro
<220> FEATURE:
<221> NAME/KEY: MISC_FEATURE
<222> LOCATION: (5)..(5)
<223> OTHER INFORMATION: Xaa is Glu
<220> FEATURE:
<221> NAME/KEY: MISC_FEATURE
<222> LOCATION: (6)..(6)
<223> OTHER INFORMATION: Xaa is Arg, Lys or Asn

<400> SEQUENCE: 23

Gly Xaa Xaa Gly Xaa Xaa
1               5

<210> SEQ ID NO 24
<211> LENGTH: 12

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid

<400> SEQUENCE: 24

Gly Xaa Xaa Gly Leu Pro Gly Glu Arg Gly Xaa Xaa
1               5                   10

<210> SEQ ID NO 25
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid

<400> SEQUENCE: 25

Gly Xaa Xaa Gly Leu Pro Gly Glu Arg Gly Xaa Xaa Gly Leu Pro Gly
1               5                   10                  15

Glu Arg

<210> SEQ ID NO 26
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(12)
<223> OTHER INFORMATION: Xaa is any amino acid
<220> FEATURE:
<221> NAME/KEY: MISC_FEATURE
<222> LOCATION: (20)..(21)
<223> OTHER INFORMATION: Xaa is any amino acid

<400> SEQUENCE: 26

Gly Xaa Xaa Gly Leu Pro Gly Glu Arg Gly Xaa Xaa Gly Leu Pro Gly
1               5                   10                  15

Glu Arg Gly Xaa Xaa Gly Leu Pro Gly Glu Arg
            20                  25
```